United States Patent [19]
Lunney et al.

[11] Patent Number: 5,922,697
[45] Date of Patent: Jul. 13, 1999

[54] COMPOUNDS, COMPOSITIONS AND METHODS FOR INHIBITING THE BINDING OF PROTEINS CONTAINING AN SH2 DOMAIN TO COGNATE PHOSPHORYLATED PROTEINS

[75] Inventors: Elizabeth A. Lunney; Kimberly S. Para, both of Ann Arbor; Mark S. Plummer, Dexter; Josyula V. N. V. Prasad, Ann Arbor; Alan R. Saltiel, Ann Arbor; Tomi Sawyer, Ann Arbor; Aurash Shahripour, Ann Arbor, all of Mich.; Juswinder Singh, Malden, Mass.; Charles J. Stankovic, Saline, Mich.

[73] Assignee: Warner-Lambert Company, Morris Plains, N.J.

[21] Appl. No.: 09/051,038

[22] PCT Filed: Oct. 2, 1996

[86] PCT No.: PCT/US96/15998

§ 371 Date: Mar. 31, 1998

§ 102(e) Date: Mar. 31, 1998

[87] PCT Pub. No.: WO97/12903

PCT Pub. Date: Apr. 10, 1997

[51] Int. Cl.$^6$ .............................. A61K 31/66; C07F 9/38; C07F 9/40
[52] U.S. Cl. .............................. 514/119; 568/190; 562/15
[58] Field of Search .............................. 558/190; 562/15; 514/119

[56] References Cited

U.S. PATENT DOCUMENTS

| | | |
|---|---|---|
| 4,853,476 | 8/1989 | Petrakis et al. . |
| 5,100,654 | 3/1992 | Pawelek et al. . |
| 5,162,311 | 11/1992 | Herrling et al. . |
| 5,175,153 | 12/1992 | Bigge et al. . |
| 5,190,921 | 3/1993 | Roques et al. . |
| 5,439,819 | 8/1995 | Littman et al. . |
| 5,580,979 | 12/1996 | Bachovchin . |

FOREIGN PATENT DOCUMENTS

| | | |
|---|---|---|
| 0524023 A1 | 1/1993 | European Pat. Off. . |
| 93/057721 | 4/1993 | WIPO . |
| 94/07913 | 4/1994 | WIPO . |
| 96/23813 | 8/1996 | WIPO . |
| 96/24343 | 8/1996 | WIPO . |

OTHER PUBLICATIONS

Songyang, Z., et al, "SH2 Domains Recognize Specific Phosphopeptide Sequences" *Cell*, Mar. 12, 1993, vol. 72:767–778.

Bilder, G.E., et al., "PDGF–Receptor Protein Tyrosine Kinase Activity (R–PTKA) in Carotoid Artery in Enhanced by Injury and Inhibited In Vivo by Tyrphostin RG 13291" *Supplement to Circulation*, Abstracts from the 65$^{th}$ Scientific Sessions, New Orleans, LA on Nov. 16–19, 1992, vol. 86, No. 4, Oct. 1992, Abstract 0675.

Bilder, G.E., et al, "Tyrosine Kinase Inhibitor (TKI), RG13291 Prevents Association of β–PDGF Receptor (β–PDGF–R) with P13Kinase in Vascular Smooth Muscle Cells (VSCM)" *Supplement to Circulation*, Abstracts form the 65$^{th}$ Scientific Sessions, New Orleans, LA, on Nov. 16–19, 1992, vol. 86, No. 4, Oct. 1992, Abstract 1160.

Graber, M., et al., "The Protein Tyrosine Kinase Inhibitor Herbimycin A, but not Genistein, Specifically Inhibits Signal Transduction by the T–cell Antigen Receptor" *International Immunology*, Jun. 1992, vol. 4, No. 11, 1201–1210.

Cohen, D.I. et al., "Participation of Tyrosine Phosphorylation in the Cytopathic Effect of Human Immunodeficiency Virus–1" *Science*, Apr. 1992, vol. 256:542–545.

Beaulieu, A.D., et al., "Nuclear Signaling in Human Neutrophils" *J of Bio Chem*, Jan. 5, 1992, vol. 267, No. 1: 426–432.

Eiseman, E. & Bolen, J.B., "Engagement of the High–affinity IgE Receptor Activates scr Protein–related Tyrosine Kinases" *Letters to Nature*, Jan. 2, 1992, vol. 355:78–80.

Margolis, B., "Proteins with SH2 Domains: Transducers in the Tyrosine Kinase Signaling Pathway" *Cell Growth & Differention*, Jan. 1992, vol. 3:73–80.

Glenney, J.R., Jr., "Tyrosine–phoshorylated Proteins: Mediators of Signal transduction from the Tyrosine Kinases" 1992, *Biochimica et Biophysica Acta*, 1134:113–127.

Paolini, R., et al., "Phosphorylation and Dephosphorylation of the High–affinity Receptor for Immunoglobulin E Immediately after Receptor Engagement and Disengagement" Oct. 31, 1991, *Nature*, vol. 353:855–858.

McColl, S.R., et al., "Involvement of Tyrosine Kinases in the Activation of Human Peripheral Blood Neutrophils by Granulocyte–Macrophage Colony–Stimulating Factor" Oct. 1, 1991, *Blood*, vol. 78, No. 7:1842–1852.

Dvir, A., et al., "The Inhibition of EGF–dependent Proliferation of Keratinocytes by Tryphostin Tyrosine Kinase Blockers" May 1991, *J of Cell Biology*, vol. 113, No. 4:857–865.

Cooke, M.P., et al., "Regulation of T Cell Receptor Signaling by a src Family Protien–Tyrosine Kinase (p59$^{fyn}$)" Apr. 19, 1991, *Cell*, vol. 65, 281–291.

Bilder, G.E., et al. "Tyrphostins Inhibits PDGF–induced DNA Synthesis and Associated Early Events in Smooth Muscle Cells" 1991, *Am J Physiol*, 260:C721–C730.

June, C.H., et al., "Inhibition of Tyrosine Phosphorylation Prevents T–cell Receptor –mediated Signal Transduction" Oct. 1990, *Proc Natl Acad Sci USA*, vol. 87:7722–7726.

*Primary Examiner*—Robert W. Ramsuer
*Attorney, Agent, or Firm*—Todd M. Crissey

[57] ABSTRACT

The present invention provides compounds that inhibit the binding of proteins containing an SH2 domain to cognate phosphorylated proteins. The invention also provides pharmaceutical compositions containing the compounds and methods of inhibiting the binding of proteins containing an SH2 domain to cognate phosphorylated proteins.

17 Claims, No Drawings

COMPOUNDS, COMPOSITIONS AND METHODS FOR INHIBITING THE BINDING OF PROTEINS CONTAINING AN SH2 DOMAIN TO COGNATE PHOSPHORYLATED PROTEINS

This application is a 371 of PCT/US96/15998, filed Oct. 2, 1996.

FIELD OF THE INVENTION

This invention relates to compounds that inhibit the binding of proteins containing an SH2 domain to cognate phosphorylated proteins. This invention also relates to pharmaceutical compositions containing the compounds and to therapeutic methods that use the compounds.

BACKGROUND OF THE INVENTION

Many of the signal transduction pathways that regulate a variety of cellular processes, including the differentiation and proliferation of normal and malignant cells, operate through phosphorylated proteins called tyrosine kinases. The two major types of tyrosine kinases are receptor and nonreceptor tyrosine kinases.

Receptor tyrosine kinases contain binding sites or receptors for growth factors such as epidermal growth factor (EGF) or platelet-derived growth factor (PDGF). When a growth factor such as EGF or PDGF binds to the receptor, the tyrosine kinase receptor protein is activated; the tyrosine kinase receptor protein is autophosphorylated; and endogenous proteins that participate in the signal transduction pathway are phosphorlyated.

Some endogenous proteins that are involved in the cellular signal transduction pathways contain a specific domain called the SH2 domain, which provides for interaction with an activated tyrosine kinase receptor protein. This interaction is a protein-protein interaction. One protein that contains an SH2 domain is pp60c-src kinase, which is also a tyrosine kinase. The pp60c-src kinase is a nonreceptor kinase and is related to a number of nonreceptor tyrosine kinases, which include, but are not limited to, Fyn, Lck, Yes, Blk, Lyn, Fgr, Hck, and Yrk. Another important protein that contains an SH2 domain is Abl.

The pp60c-src protein is exemplary of the Src family of tyrosine kinases. The pp60c-src has three major domains: SH1, SH2, and SH3. The SH1 domain is most commonly called the catalytic domain or tyrosine kinase domain. The SH3 domain is a binding region for proteins having proline-rich sequences. Both the SH2 and SH3 domains are noncatalytic, but are important in protein-protein recognition.

The Src family of protein kinases, which all contain a SH2 domain, are involved in a number of cellular signalling pathways. For example, Src is involved in growth factor receptor signalling; integrin-mediated signaling; T- and B-cell activation and osteoclast activation. It is known that the Src SH2 domain binds to several key receptor and nonreceptor tyrosine kinases such as tyrosine kinases containing receptors for PDGF, EGF, HER2/Neu (an oncogene form of EGF), Fibroblast growth factor, focal adhesion kinase, p130 protein, and p68 protein. In addition, pp60c-src has been shown to be involved in the regulation of DNA synthesis, mitosis, and other cellular activities.

Thus, it would be useful to have compounds that inhibit the binding of proteins containing an SH2 domain to cognate phosphorylated proteins, as the inhibition of binding of proteins containing an SH2 domain to cognate phosphorylated proteins can be used to treat proliferative diseases such as cancer, osteoporosis, inflammation, allergy, restenosis, and cardiovascular disease, which all rely on signal transduction involving proteins that contain an SH2 domain that binds to phosphorylated proteins during the cellular signalling process.

SUMMARY OF THE INVENTION

The present invention provides compounds having the Formula I

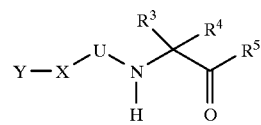

wherein
U is —CO—, —CS—, —SO—, or —SO$_2$;
Y is

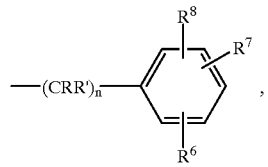

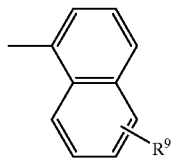

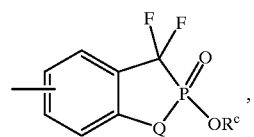

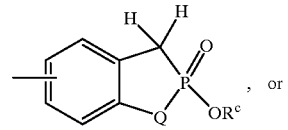

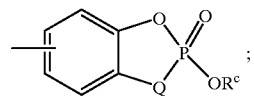

, or

X is R$^1$R$^2$C

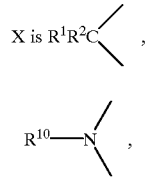

or a bond;
R$^1$ is hydrogen, RCONR'—, RR'NCONR"—, RSO$_2$NR'—, RCSNR'—, RR'NCSNR"—, RR'NSO$_2$NR"—, ROCONR'—, or

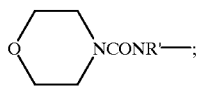

R² is hydrogen, alkyl, cycloalkyl-(CH₂)ₙ—, substituted alkyl, aryl-(CH₂)ₙ—, heteroaryl-(CH₂)ₙ—, —(CH₂)ₙ—CO₂H, substituted cycloalkyl-(CH₂)ₙ—, substituted aryl-(CH₂)ₙ—, or substituted heteroaryl-(CH₂)ₙ—;

R³ is hydrogen, alkyl, cycloalkyl-(CH₂)ₙ—, substituted alkyl, aryl-(CH₂)ₙ—, heteroaryl-(CH₂)ₙ—, —(CH₂)ₙ—CO₂H, substituted cycloalkyl-(CH₂)ₙ—, substituted aryl-(CH₂)ₙ—, or substituted heteroaryl-(CH₂)ₙ—;

R⁴ is hydrogen or alkyl;

R⁵ is —NRR',

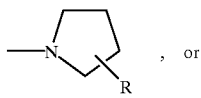, or

;

R⁶ and R⁹ are independently —OPO₃RᶜRᵈ, —CF₂PO₃RᶜRᵈ, —CH₂PO₃RᶜRᵈ, —PO₃RᶜRᵈ, —SO₃Rᶜ, —OSO₃Rᶜ, —CH₂SO₃Rᶜ, —SO₂NH₂, —OSO₂NH₂, or —CH₂SO₂NH₂;

R⁷ and R⁸ are independently hydrogen, alkyl, substituted alkyl, halogen, —OR, —NRR', —COCF₃, —(CH₂)ₙCH₂OH, —(CH₂)ₙCO₂H, —(CH₂)ₙCHO, —(CH₂)ₙNRR', or —Q—CH₂—(CH₂)ₙ—NRR';

R¹⁰ is —(CH₂)ₙCO₂H, hydrogen, alkyl, aryl, substituted alkyl, or —(CH₂)ₙ-substituted aryl;

Rᶜ and Rᵈ are independently —R, —CH₂CH₂Z, —CH₂CHZ₂, —CH₂CZ₃, or

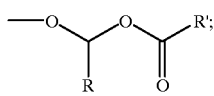

Q is —O—, —NH—, —S—, —CH₂O—, —CH₂NH—, or —CH₂S—;

Z is —Cl, —Br, or —F;

R, R', and R" are independently hydrogen, alkyl, cycloalkyl-(CH₂)ₙ—, aryl-(CH₂)ₙ—, heteroaryl-(CH₂)ₙ—, substituted alkyl, substituted cycloalkyl-(CH₂)ₙ—, substituted aryl-(CH₂)ₙ—, —(CH₂)ₙCO₂H, or substituted heteroaryl-(CH₂)ₙ; and each n is independently 0 to 5, or the pharmaceutically acceptable salts, amides, esters, or prodrugs thereof.

In a preferred embodiment of the compounds of Formula I,

U is —CO—;

X is R¹R²C< and

Y is

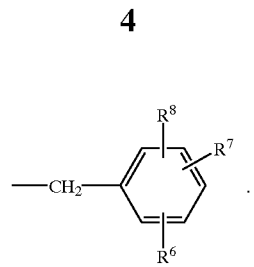

In a preferred embodiment of the compounds of Formula I,

U is —CO—;

X is R¹R²C< and

Y is

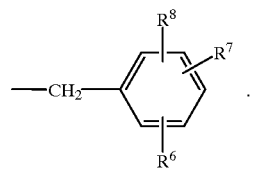

R¹ is RCONR'—, —NRCONR'R", —NRSO₂R', or

R², R⁴, R⁷, and R⁸ are hydrogen;
R³ is —(CH₂)ₙCO₂H, alkyl, or —(CH₂)ₙ-substituted aryl;
R⁵ is —NRR',

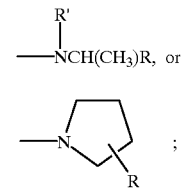

and
R⁶ is —OPO₃RᶜRᵈ, —CF₂PO₃RᶜRᵈ, or —PO₃RᶜRᵈ.

In another preferred embodiment of the compounds of Formula I

U is —CO—;

X is R¹R²C< and

Y is

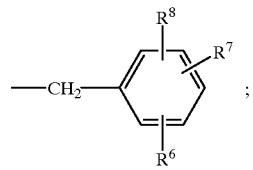

R¹ is CH₃CONH—;
R², R⁴, R⁷, and R⁸ are hydrogen;
R³ is —CH₂CH₂CO₂H;

$R^5$ is —NRR',

or

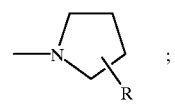

;

and $R^6$ is —OPO$_3$R$^c$R$^d$, —CF$_2$PO$_3$R$^c$R$^d$, or —PO$_3$R$^c$R$^d$.

In another preferred embodiment of the compounds of Formula I

U is —CO—;

Y is

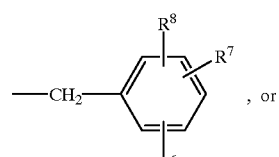

, or

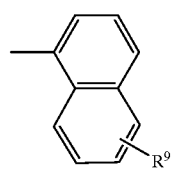

and

X is

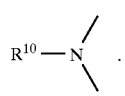

.

In another preferred embodiment of the compounds of Formula I

U is —CO—;

Y is

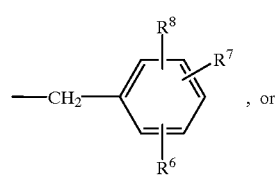

, or

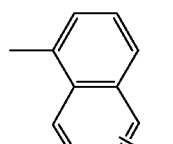

;

X is

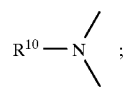

;

$R^3$ and $R^{10}$ are —(CH$_2$)$_n$CO$_2$H;
$R^4$ is hydrogen;
$R^5$ is —NRR',

or

;

$R^7$ and $R^8$ are hydrogen; and
$R^6$ is —OPO$_3$R$^c$R$^d$, —CF$_2$PO$_3$R$^c$R$^d$, or —PO$_3$R$^c$R$^d$.

In another aspect, the present invention provides the compounds of Formula II below:

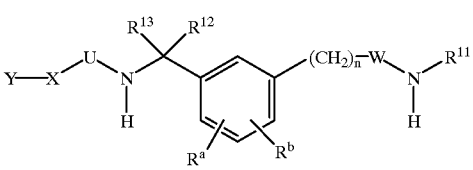

II wherein U and W are independently —CO—, —CS—, —SO—, or —SO$_2$—;

Y is

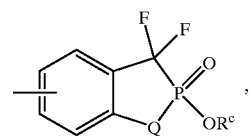

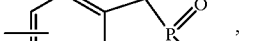

, or

;

X is R$^{19}$R$^{20}$C<, R$^{18}$—N<, or a bond;
R$^{11}$ is hydrogen, alkyl, —OH, substituted alkyl, or —NH$_2$;
R$^{12}$ is hydrogen or alkyl;
R$^{13}$ is —(CH$_2$)$_n$CO$_2$H, alkyl, —(CH$_2$)$_n$-aryl, —(CH$_2$)$_n$-heteroaryl, —(CH$_2$)$_n$-cycloalkyl, hydrogen, substituted cycloalkyl-(CH$_2$)$_n$—, substituted aryl-(CH$_2$)$_n$—, substituted heteroaryl-(CH$_2$)$_n$—, or substituted alkyl;

$R^{14}$ and $R^{17}$ are independently —$OPO_3R^cR^d$, —$CF_2PO_3R^cR^d$, —$CH_2PO_3R^cR^d$, —$PO_3R^cR^d$, —$SO_3R^c$, —$OSO_3R^c$, —$CH_2SO_3R^c$, —$SO_2NH_2$, —$OSO_2NH_2$, or —$CH_2SO_2NH_2$;

$R^{15}$ and $R^{16}$ are independently hydrogen, alkyl, halogen, —OR, —NRR', —$COCF_3$, —$(CH_2)_nCH_2OH$, —$(CH_2)_nCO_2H$, —$(CH_2)_nNRR'$, —$(CH_2)_nCHO$, or —Q—$CH_2$—$(CH_2)_n$—NRR';

$R^{18}$ is —$(CH_2)_nCO_2R$, hydrogen, alkyl, —$(CH_2)_n$CONRR', substituted alkyl, or —$(CH_2)_n$-substituted aryl;

$R^{19}$ is hydrogen, RCONR'—, RR'NCONR"—, $RSO_2NR'$—, $RR'NSO_2NR"$—, ROCONR'—, or

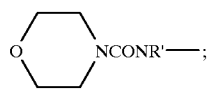

$R^{20}$ is hydrogen, alkyl, cycloalkyl-$(CH_2)_n$—, substituted alkyl, aryl-$(CH_2)_n$—, heteroaryl-$(CH_2)_n$—, —$(CH_2)_n$—$CO_2H$, substituted cycloalkyl-$(CH_2)_n$—, substituted aryl-$(CH_2)_n$—, or substituted heteroaryl-$(CH_2)_n$—;

$R^a$ is hydrogen, halogen, or alkyl;

$R^b$ is hydrogen, alkyl, —OR, —$O(CH_2)_n$-aryl, —NRR', —$O(CH_2)_n$-substituted alkyl, —SR, —$O(CH_2)_n$-substituted aryl, or —$O(CH_2)_n$-cycloalkyl;

$R^c$ and $R^d$ are independently —R, —$CH_2CH_2Z$, —$CH_2CHZ_2$, —$CH_2CZ_3$, or

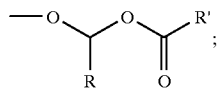

Q is —O—, —NH—, —S—, —$CH_2O$—, —$CH_2NH$—, or —$CH_2S$—;

Z is —Cl, —Br, or —F;

R, R', and R" are independently hydrogen, alkyl, cycloalkyl-$(CH_2)_n$—, aryl-$(CH_2)_n$—, heteroaryl-$(CH_2)_n$—, —$CH_2$—$(CH_2)_n$—$CO_2H$, substituted cycloalkyl-$(CH_2)_n$—, substituted alkyl, substituted aryl-$(CH_2)_n$—, or substituted heteroaryl-$(CH_2)_n$—; and each n is independently 0 to 5, or the pharmaceutically acceptable salts, amides, esters, or prodrugs thereof.

In a preferred embodiment of the compounds of Formula II
Y is

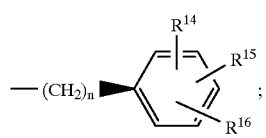

U and W are —CO—; and
X is a bond.

In another preferred embodiment of the compounds of Formula II,

Y is

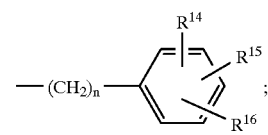

U and W are —CO—;
X is a bond;
$R^{13}$, $R^a$, $R^{15}$, and $R^{16}$ are hydrogen;
$R^{12}$ and $R^{11}$ are hydrogen or alkyl;
$R^b$ is —OR, —$O(CH_2)_n$-aryl, —$O(CH_2)_n$ substituted aryl, or —$O(CH_2)_n$cycloalkyl; and
$R^{14}$ is —$OPO_2R^cR^d$ or —$CF_2PO_3R^cR^d$.

In another preferred embodiment of the compounds of Formula II,
X is $R^{19}R^{20}C<$;
Y is

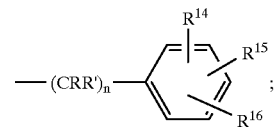

and
U and W are —CO—.

In another preferred embodiment of the compounds of Formula II,
X is $R^{19}R^{20}C<$;
Y is

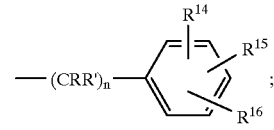

U and W are —CO—;
$R^{19}$ is RCONR'— or RR'NCONR"—;
$R^{20}$, $R^{15}$, $R^{13}$, $R^{11}$, $R^a$, and $R^{16}$ are hydrogen;
$R^{12}$ is alkyl or hydrogen;
$R^b$ is —OR, —$O(CH_2)_n$-aryl, —$O(CH_2)_n$ substituted aryl, or —$O(CH_2)_n$cycloalkyl; and
$R^{14}$ is —$OPO_3R^cR^d$ or —$CF_2PO_3R^cR^d$.

Also provided by the present invention is method of inhibiting the binding of a protein containing an SH2 domain to a cognate phosphorylated protein, the method comprising administering to a patient in need of SH2 inhibition an SH2 inhibiting amount of a compound of Formula I or II.

In another aspect, the present invention provides a pharmaceutical composition that comprises a compound of Formula I or II and a pharmaceutically acceptable carrier.

In another aspect, the present invention provides a method of treating a patient having a proliferative disease, the method comprising administering to the patient a therapeutically effective amount of a compound of Formula I or II.

In another aspect, the present invention provides a method of treating a patient having cancer, the method comprising administering to the patient a therapeutically effective amount of a compound of Formula I or II.

In another aspect, the present invention provides a method of treating a patient having restenosis, the method comprising administering to the patient a therapeutically effective amount of a compound of Formula I or II.

In another aspect, the present invention provides a method of treating a patient having osteoporosis, the method comprising administering to the patient a therapeutically effective amount of a compound of Formula I or II.

In another aspect, the present invention provides a method of treating a patient having inflammation, the method comprising administering to the patient a therapeutically effective amount of a compound of Formula I or II.

In another aspect, the present invention provides a method of treating a patient having allergies, the method comprising administering to the patient a therapeutically effective amount of a compound of Formula I or II.

In another aspect, the present invention provides a method of treating a patient having cardiovascular disease, the method comprising administering to the patient a therapeutically effective amount of a compound of Formula I or II.

DETAILED DESCRIPTION OF THE INVENTION

This invention provides compounds that inhibit the binding of proteins containing an SH2 domain with cognate phosphorylated proteins. One group of compounds of the present invention have the Formula I

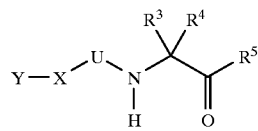

wherein
U is —CO—, —CS—, —SO—, or —SO$_2$—;
Y is

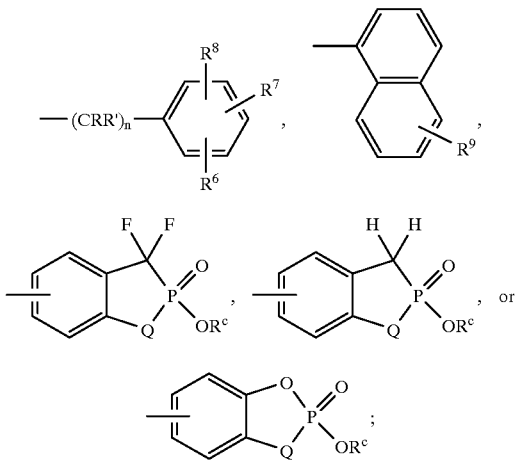

X is R$^1$R$^2$C<, R$^{10}$—N<, or a bond;
R$^1$ is hydrogen, RCONR'—, RR'NCONR"—, RSO$_2$NR'—, RCSNR'—, RR'NCSNR"—, RR'NSO$_2$NR"—, ROCONR'—, or

R$^2$ is hydrogen, alkyl, cycloalkyl-(CH$_2$)$_n$—, substituted alkyl, aryl-(CH$_2$)$_n$—, heteroaryl-(CH$_2$)$_n$—, —(CH$_2$)$_n$—CO$_2$H, substituted cycloalkyl-(CH$_2$)$_n$—, substituted aryl-(CH$_2$)$_n$—, or substituted heteroaryl-(CH$_2$)$_n$—;

R$^3$ is hydrogen, alkyl, cycloalkyl-(CH$_2$)$_n$—, substituted alkyl, aryl-(CH$_2$)$_n$—, heteroaryl-(CH$_2$)$_n$—, —(CH$_2$)$_n$—CO$_2$H, substituted cycloalkyl-(CH$_2$)$_n$—, substituted aryl-(CH$_2$)$_n$—, or substituted heteroaryl-(CH$_2$)$_n$—;

R$^4$ is hydrogen or alkyl;
R$^5$ is —NRR',

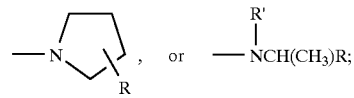

R$^6$ and R$^9$ are independently —OPO$_3$R$^c$R$^d$, —CF$_2$PO$_3$R$^c$R$^d$, —CH$_2$PO$_3$R$^c$R$^d$, —PO$_3$R$^c$R$^d$, —SO$_3$R$^c$, —OSO$_3$R$^c$, —CH$_2$SO$_3$R$^c$, —SO$_2$NH$_2$, —OSO$_2$NH$_2$, or —CH$_2$SO$_2$NH$_2$;

R$^7$ and R$^8$ are independently hydrogen, alkyl, substituted alkyl, halogen, —OR, —NRR', —COCF$_3$, —(CH$_2$)$_n$CH$_2$OH, —(CH$_2$)$_n$CO$_2$H, —(CH$_2$)$_n$CHO, —(CH$_2$)$_n$NRR', or —Q—CH$_2$—(CH$_2$)$_n$—NRR';

R$^{10}$ is —(CH$_2$)$_n$CO$_2$H, hydrogen, alkyl, aryl, substituted alkyl, or —(CH$_2$)$_n$-substituted aryl;

R$^c$ and R$^d$ are independently —R, —CH$_2$CH$_2$Z, —CH$_2$CHZ$_2$, —CH$_2$CZ$_3$, or

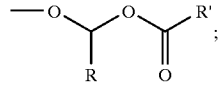

Q is —O—, —NH—, —S—, —CH$_2$O—, —CH$_2$NH—, or —CH$_2$S—;

Z is —Cl, —Br, or —F;

R, R', and R" are independently hydrogen, alkyl, cycloalkyl-(CH$_2$)$_n$—, aryl-(CH$_2$)$_n$—, heteroaryl-(CH$_2$)$_n$—, substituted alkyl, substituted cycloalkyl-(CH$_2$)$_n$—, substituted aryl-(CH$_2$)$_n$—, —(CH$_2$)$_n$CO$_2$H, or substituted heteroaryl-(CH$_2$)$_n$—; and each n is independently 0 to 5, or the pharmaceutically acceptable salts, amides, esters, or prodrugs thereof.

Another group has the Formula II below:

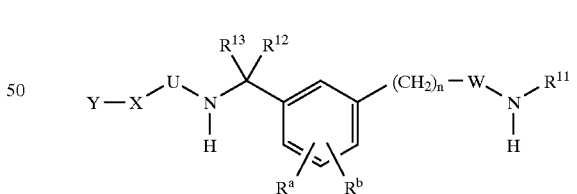

wherein U and W are independently —CO—, —CS—, —SO—, or —SO$_2$—;
Y is

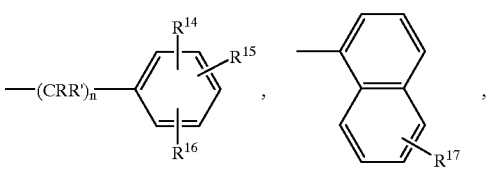

-continued

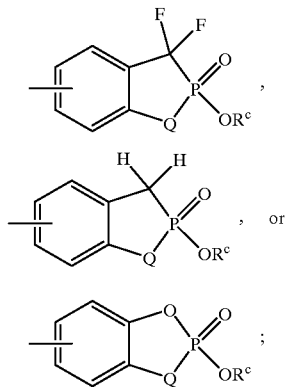

X is $R^{19}R^{20}C<$, $R^{18}$—N<, or a bond;
$R^{11}$ is hydrogen, alkyl, —OH, substituted alkyl, or —NH$_2$;
$R^{12}$ is hydrogen or alkyl;
$R^{13}$ is —(CH$_2$)$_n$CO$_2$H, alkyl, —(CH$_2$)$_n$-aryl, —(CH$_2$)$_n$-heteroaryl, —(CH$_2$)$_n$-cycloalkyl, hydrogen, substituted cycloalkyl-(CH$_2$)$_n$—, substituted aryl-(CH$_2$)$_n$—, substituted heteroaryl-(CH$_2$)$_n$—, or substituted alkyl;
$R^{14}$ and $R^{17}$ are independently —OPO$_3$R$^c$R$^d$, —CF$_2$PO$_3$R$^c$R$^d$, —CH$_2$PO$_3$R$^c$R$^d$, —PO$_3$R$^c$R$^d$, —SO$_3$R$^c$, —OSO$_3$R$^c$, —CH$_2$SO$_3$R$^c$, —SO$_2$NH$_2$, —OSO$_2$NH$_2$, or —CH$_2$SO$_2$NH$_2$;
$R^{15}$ and $R^{16}$ are independently hydrogen, alkyl, halogen, —OR, —NRR', —COCF$_3$, —(CH$_2$)$_n$CH$_2$OH, —(CH$_2$)$_n$CO$_2$H, —(CH$_2$)$_n$NRR', —(CH$_2$)$_n$CHO, or —Q—CH$_2$—(CH$_2$)$_n$—NRR';
$R^{18}$ is —(CH$_2$)$_n$CO$_2$R, hydrogen, alkyl, —(CH$_2$)$_n$CONRR', substituted alkyl, or —(CH$_2$)$_n$-substituted aryl;
$R^{19}$ is hydrogen, RCONR'—, RR'NCONR"—, RSO$_2$NR'—, RR'NSO$_2$NR"—, ROCONR'—, or

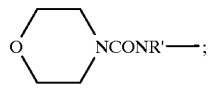

$R^{20}$ is hydrogen, alkyl, cycloalkyl-(CH$_2$)$_n$—, substituted alkyl, aryl-(CH$_2$)$_n$—, heteroaryl-(CH$_2$)$_n$—, —(CH$_2$)$_n$—CO$_2$H, substituted cycloalkyl-(CH$_2$)$_n$—, substituted aryl-(CH$_2$)$_n$—, or substituted heteroaryl-(CH$_2$)$_n$—;
$R^a$ is hydrogen, halogen, or alkyl;
$R^b$ is hydrogen, alkyl, —OR, —O(CH$_2$)$_n$-aryl, —NRR', —O(CH$_2$)$_n$-substituted alkyl-, —SR, —O(CH$_2$)$_n$-substituted aryl, or —O(CH$_2$)$_n$-cycloalkyl;
$R^c$ and $R^d$ are independently —R, —CH$_2$CH$_2$Z, —CH$_2$CHZ$_2$, —CH$_2$CZ$_3$, or

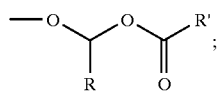

Q is —O—, —NH—, —S—, —CH$_2$O—, —CH$_2$NH—, or —CH$_2$S—;
Z is —Cl, —Br, or —F;
R, R', and R" are independently hydrogen, alkyl, cycloalkyl-(CH$_2$)$_n$—, aryl-(CH$_2$)$_n$—, heteroaryl-(CH$_2$)$_n$—, —CH$_2$—(CH$_2$)$_n$—CO$_2$H, substituted cycloalkyl-(CH$_2$)$_n$—, substituted alkyl, substituted aryl-(CH$_2$)$_n$—, or substituted heteroaryl-(CH$_2$)$_n$—; and each n is independently 0 to 5, or the pharmaceutically acceptable salts, amides, esters, or prodrugs thereof.

The term "alkyl" means a straight or branched chain hydrocarbon. Preferably, the alkyl group has from 1 to 10 carbon atoms. More preferably, the alkyl group has from 1 to 6 carbon atoms. Examples of alkyl groups include, but are not limited to, methyl, ethyl, propyl, butyl, pentyl, hexyl, isopropyl, isobutyl, and tert-butyl.

The term "cycloalkyl" means a cyclic hydrocarbon, which can be saturated or unsaturated. Preferably, the cycloalkyl group has from 3 to 10 carbon atoms. More preferably, the cycloalkyl group has from 3 to 6 carbon atoms. Examples of cycloalkyl groups include, but are not limited to, cyclopropane, cyclobutane, cyclopentane, cyclopentene, cyclohexane, cyclohexene, cycloheptane, cyclooctane, and adamantane.

The term "aryl" means a cyclic aromatic hydrocarbon. Examples of aryl groups include, but are not limited to, phenyl and naphthyl.

The term "heteroaryl" means a cyclic aromatic hydrocarbon that contains one or more heteroatom. Examples of heteroatoms include, but are not limited to, oxygen, nitrogen, and sulfur. Examples of heteroaryl groups include, but are not limited to, pyridinyl, furanyl, thiophenyl, and pyrrolyl.

The terms substituted aryl, substituted phenyl, substituted cycloalkyl, substituted heteroaryl, or substituted alkyl mean an aryl, phenyl, cycloalkyl, heteroaryl, or alkyl group that has one or more substituent. Examples of substituents include alkyl, alkoxy, (such as methoxy, ethoxy, or tert-butoxy), halogen, —NO$_2$, —OCH$_2$CONH$_2$, —OCH$_2$CO$_2$H, —SO$_3$H, —CONH$_2$, —SO$_2$NH$_2$, or —CH$_2$OH, and the like.

The symbol "—" means a bond.

Examples of proteins that contain an SH2 domain include, but are not limited to, Src, Fyn, Lck, Yes, Blk, Lyn, Fgr, Hck, Yrk, and Abl. Preferably, the protein is Src, and most preferably the protein is pp60c-src.

The term "cognate phosphorylated protein" means a protein to which the SH2 domain of a protein containing an SH2 domain binds or is associated. Examples of cognate phosphorylated proteins include, but are not limited to, PDGF receptor protein, EGF receptor protein, HER2/Neu receptor protein (an oncogene form of EGF receptor protein), fibroblast growth factor receptor protein, focal adhesion kinase protein, p130 protein, and p68 protein.

The compounds and pharmaceutically acceptable compositions that contain the compounds can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions, or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.,* 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods. Particularly preferred esters are phosphoesters. Examples of suitable phosphoesters include, but are not limited to —$PO_3R^cR^d$, —$CF_2PO_3R^cR^d$, and —$CH_2PO_3R^cR^d$, where $R^c$ and $R^d$ are as defined above. (See, for example, Jones R. J. and Bischofberger N., "Minireview: nucleotide prodrugs", *Antiviral Research,* 1995;27:1–17, which is incorporated herein by reference.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amides and $C_1$–$C_2$ dialkyl secondary amides are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient at dosage levels in the range of about 1 to about 7,000 mg/day. For a normal human adult having a body weight of about 70 kg, a dosage in the range of about 1 to about 100 mg/kg of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The compounds of the present invention can exist in different stereoisometric forms by virtue of the presence of asymmetric centers in the compounds. It is contemplated that all stereoisometric forms of the compounds as well as mixture thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention and are not intended to limit the specification or the claims in any manner.

EXAMPLES

The following abbreviations may be used in the present application:

| | |
|---|---|
| Abu | α-Aminobutyric acid |
| Ac | Acetyl |
| Ala | Alanine |
| Arg | Arginine |
| Asn | Asparginine |
| Asp | Aspartic acid |
| Boc | Tertiary butyloxycarbonyl |
| Bn | Benzyl |
| Cbz | Benzyloxycarbonyl |
| Cys | Cysteine |
| $CF_3SO_2H$ | Trifluoromethanesulfonic acid |
| DCC | N,N'-Dicyclohexylcarbodiimide |
| DCM | Dichloromethane |
| DIC | N,N'-Diisopropylcarbodiimide |
| DIEA | N,N'-Diisopropylethylamine |
| DMAP | 4-Dimethylaminopyridine |
| DMF | N,N'-Dimethylformamide |
| EDCI | N-Ethyl-N'-Dimethylaminopropyl-carbodiimide |

-continued

| | |
|---|---|
| EtOAc | Ethyl acetate |
| $Et_2O$ | Diethyl ether |
| Fmoc | 9-Fluorenylmethyloxycarbonyl |
| Gln | Glutamine |
| Glu | Glutamic acid |
| Gly | Glycine |
| Hcl | Hydrochloric acid |
| His | Histidine |
| HOAc | Acetic acid |
| HOBT | 1-Hydroxybenzotriazole |
| Ile | Isoleucine |
| iprOH | Isopropanol |
| KOH | Potassium hydroxide |
| Leu | Leucine |
| Lys | Lysine |
| MeCN | Acetonitrile |
| MeOH | Methanol |
| Met | Methionine |
| NHOS | N-Hydroxysuccinimide |
| NMP | N-Methylpyrrolidone |
| Phe | Phenylalanine |
| Pro | Proline |
| rt | Retention time |
| Ser | Serine |
| TFA | Trifluoroacetic acid |
| THF | Tetrahydrofuran |
| Thr | Threonine |
| Trp | Tryptophan |
| Tyr | Tyrosine |
| Val | Valine |

EXAMPLE 1

[S-(R*,R*)]-4-[2-Acetylamino-3-(4-phosphonooxy-phenyl)-propionylamino]-4-[(3-cyclohexyl-propyl)-methylcarbamoyl]-butyric acid or Ac-(O-phosphono)-L-Tyr-L-Glu-N(methyl) (3-cyclohexylpropyl)

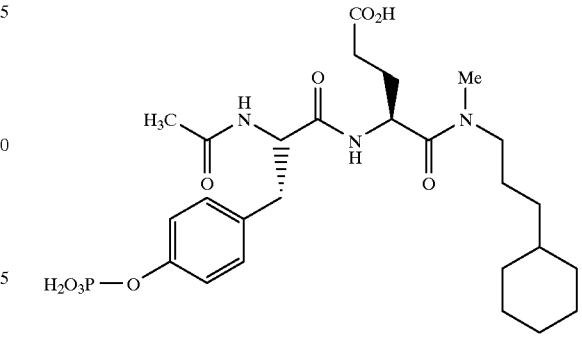

Step 1: Fmoc-L-Glu(OtBu)-N(methyl)(3-cyclohexylpropyl)

To methyl (3-cyclohexylpropyl) amine hydrochloride (5.0 mmol, 960 mg) in tetrahydrofuran (20 mL) was added Fmoc-L-Glu(OtBu) (5.5 mmol, 2.34 g) followed by sequential addition of 1-hydroxybenzotriazole (6.25 mmol, 845 mg), N-methylmorpholine (12.5 mmol, 1.37 mL), and 1-(3-dimethylaminopropyl)-3-ethylcarbodiimide hydrochloride (6.25 mmol, 1.2 g). After stirring 16 hours at room temperature, diethyl ether was added, and the remaining residue was dissolved in water. The mixture was separated, washed with 10% sulfuric acid, water, then saturated sodium bicarbonate, and then brine to provide product as a colorless foam (2.59 g, 92%). $^1$H NMR ($CDCl_3$, 300 MHz): δ 0.87 (m, 2H), 1.17 (m, 6H), 1.46 (s, 9H), 1.50–1.80 (m, 8H), 2.05 (m, 1H), 2.33 (m, 2H), 2.95–3.11 (s, 3H, rotational isomers), 3.18–3.58 (m, 2H), 4.21 (t, 1H), 4.36 (m, 2H), 4.70 (m, 1H), 5.80 (dd, 1H), 7.27–7.45 (m, 4H), 7.60 (m, 2H), 7.77 (d, 2H); IR ($CHCl_3$): 1719, 1642 $cm^{-1}$; Mass Spectrum (Chemical Ionization, 1% $NH_3$ in $CH_4$) m/z 563(M+H).

Step 2: Ac-L-Tyr-L-Glu(OtBu)-N(methyl) (3-cyclohexylpropyl)

To Fmoc-L-Glu(OtBu)-N(methyl) (3-cyclohexylpropyl) (2.0 mmol, 1.12 g) in dichloromethane (20 mL) was added piperidine (4 mL). After 20 minutes, toluene (20 mL) was added, and the solvent was removed under reduced pressure. Toluene (20 mL) was again added, and the solvent was evaporated. The resulting residue was dissolved in tetrahydrofuran (15 mL) and coupled with Ac-L-Tyr (2.2 mmol, 491 mg) in the manner described above to give a solid residue upon work-up. Chromatography of the residue (3:7, tetrahydrofuran/dichloromethane) gave product as a colorless foam (880 mg, 81%). $^1$H NMR (DMSO, 300 MHz): δ 0.85 (m, 2H), 1.03–1.30 (m, 6H), 1.40 (s, 9H), 1.40–1.90 (m, 10H), 1.75 (s, 3H), 2.20 (t, 3H), 2.60 (dd, 1H), 2.78–2.95 (s, 3H, rotational isomers), 3.10–3.30 (m, 2H), 4.44 (m, 1H), 4.70 (m, 1H), 6.61 (d, 2H), 7.00 (d, 2H), 7.96 (d, 1H), 8.01 (t, 3H), 9.15 (s, 1H); IR (CHCl$_3$): 1720, 1639 cm$^{-1}$; Mass Spectrum (Chemical Ionization, 1% NH$_3$ in CH$_4$) m/z 546 (M+H).

Step 3: Ac-(O-phosphono)-L-Tyr-L-Glu-N(methyl) (3-cyclohexylpropyl)

To Ac-L-Tyr-L-Glu(OtBu)-N(methyl) (3-cyclohexylpropyl) (0.40 mmol, 218 mg) in dichloromethane (5 mL) was added tetrazole (0.80 mmol, 56 mg) and di-tert-butyl diethylphosphoramidate (0.60 mmol, 0.17 mL). After 3 hours, thin layer analysis indicated the reaction was complete and tert-butylhydroperoxide (2.4 mmol, 0.22 mL) was added. After 2 hours, ethyl acetate was added, and the organic phase was washed with 10% sulfuric acid, water, 2% sodium hydroxide, and then saturated sodium chloride. The solvent was removed under reduced pressure to give an oil (432 mg). This oil was treated with trifluoroacetic acid (15 mL) and water (1 mL) for 1 hour. The solvent was removed under reduced pressure, and the residue was precipitated with diethyl ether to give a colorless solid. Preparative HPLC of crude product (75 mg) employing a Vydac C18 (22×250 mm) column eluting with a gradient of 0% to 30% acetonitrile containing 0.1% trifluoroacetic acid and water containing 0.1% trifluoroacetic acid (TFA) provided pure product after lyophilization (31 mg). HPLC 100%, rt=17.3 minutes, C18 (analytical column, Vydac, 4.6×250 mm), eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 569.5 (M–H).

EXAMPLE 2

4-[(S)-2-Acetylamino-3-(4-phosphonooxy-phenyl)-(S)-propionylamino]-4-(2-cyclohexyl-(S)-1-methylethylcarbamoyl)-butyric acid or Ac-(O-phosphono)-L-Tyr-L-Glu-NH((S)-2-cyclohexyl-1-methylethyl)

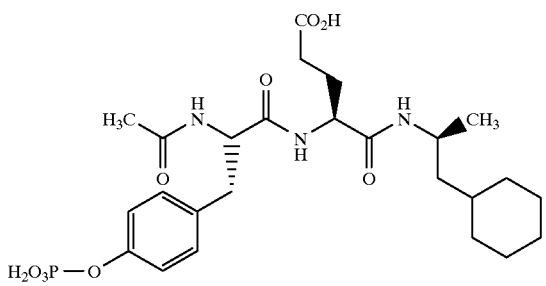

The title compound was synthesized in a manner similar to that described for Example 1. Product was obtained as a colorless solid (160 mg). HPLC 100%, rt=16.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 555.4 (M–H).

EXAMPLE 3

4-[(S)-2-Acetylamino-3-(4-phosphonooxy-phenyl)-(S)-propionyl-amino]-4-(2-cyclohexyl-(S)-1-methyl-ethyl)-methyl-carbamoyl)-butyric acid or Ac-(O-phosphono)-L-Tyr-L-Glu-N(methyl)((S)-2-cyclohexyl-1-methylethyl)

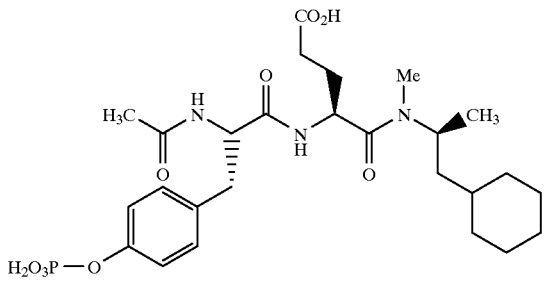

The title compound was synthesized in a manner similar to that described for Example 1. Product was obtained as a colorless solid (117 mg). HPLC 93%, rt=17.5 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 569.5 (M–H).

EXAMPLE 4

4-{(RS)-2-Acetylamino-3-[4-(difluoro-phosphono-methyl)-phenyl]-(S)-propionylamino}-4-[(3-cyclohexyl-propyl)-methyl-carbamoyl]-butyric acid or Ac-(4-(difluorophosphonomethyl))-D/L-Phe-L-Glu-N(methyl) (3-cyclohexylpropyl)

19

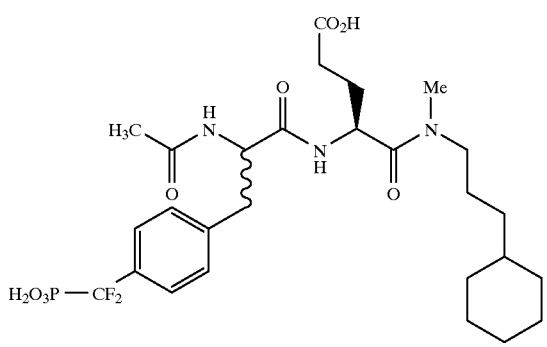

Step 1: Boc-[4-(diethoxyphosphonyl)-difluoromethyl]-D/L-Phe Benzyl ester

Boc-[4-(diethoxyphosphonyl)-difluoromethyl]-D/L-Phe Benzyl ester can be prepared in accordance with methods well known to those skilled in the art. (See, for example, Burke, et al., *J. Org. Chem.,* 1993;58(6):1336–1340.)

Step 2: Ac-[4-(diethoxyphosphonyl)-difluoromethyl]-D/L-Phe

Ac-[4-(diethoxyphosphonyl)difluoromethyl]-D/L-Phe was prepared in a manner similar to that described for Example 5 (Step 1).

Step 3: Ac-(4-(difluorophosphonomethyl))-D/L-Phe-L-Glu-N(methyl)(3-cyclohexylpropyl)

The title compound was then synthesized in a manner similar with the substitution of Example 1, Ac-[4-(diethoxyphosphonyl)-difluoromethyl]-D/L-Phe for Ac-L-Tyr. The crude peptide was deprotected with trifluoroacetic acid/trimethysilyl triflate/ethanedithiol/m-cresol/dimethylsulfide (4/1/0.1/0.003/1) for 2 hours at room temperature. Careful addition of water then ether quenched the reaction. Preparative HPLC, as previously described, of the aqueous layer provided product as a colorless solid after lyophilization (29 mg). HPLC 93%, rt=15.1 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 603.4 (M–H).

EXAMPLE 5

[S-(R*,R*)]-4-{2-Acetylamino-3-[4-(difluoro-phosphonomethyl)-phenyl]-propionylamino}-4-[(3-cyclohexylpropyl)-methyl-carbamoyl]-butyric acid or Ac-(4-(difluorophosphonomethyl))-L-Phe-L-Glu-N(methyl) (3-cyclohexylpropyl)

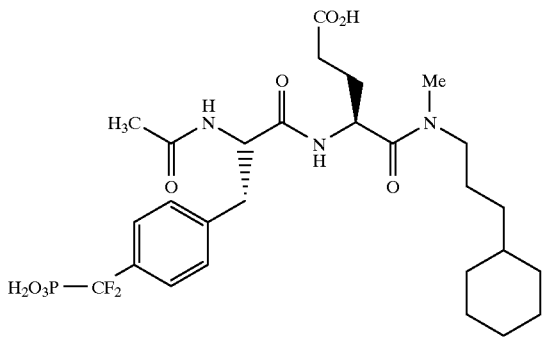

20

Step 1: Ac-[4-(diethoxyphosphonyl)-difluoromethyl]-L-Phe

Boc-[4-(diethoxyphosphonyl)-difluoromethyl]-L-Phe Benzyl ester can be prepared in accordance with methods well known to those skilled in the art. (See, for example, Smythe and Burke, *Tett. Lett.,* 1994;35(4):551–554.) Boc-[4-(diethoxyphosphonyl)-difluoromethyl]-L-Phe Benzyl ester (1.75 mmol, 950 mg) was deprotected with 20 mL trifluoroacetic acid:dichloromethane (1:1) for 5 hours at 0° C. The reaction was diluted with 200 mL of ethyl acetate and washed with saturated sodium bicarbonate then saturated sodium chloride, dried with sodium sulfate, filtered, and concentrated under reduced pressure to yield 795 mg of a colorless oil. The crude oil was treated with acetic anhydride (10 mmol, 944 μL) and pyridine (15 mmol, 1.21 mL) in 20 mL dichloromethane for 4 hours at room temperature then 2 days at 4° C. The reaction was diluted with 400 mL of ethyl acetate and washed with saturated sodium bicarbonate, 5% hydrochloric acid, saturated sodium bicarbonate, then saturated sodium chloride, dried with sodium sulfate, filtered, and concentrated under reduced pressure to yield 1.2 g of a pale yellow oil. Chromatography of the residue (20:1, dichloromethane:methanol) gave 719 mg (85%) of the product as a colorless oil. Removal of the benzyl ester with hydrogen and palladium on carbon (20%) in ethanol gave, after filtration and concentrating under reduced pressure, 564 mg (99%) of a solid foam. $^1$H NMR (DMSO, 400 MHz): δ 1.20 (t, 6H), 1.76 (s, 3H), 2.90 (dd, 1H), 3.12 (dd, 1H), 4.07 (m, 4H), 4.44 (m, 1H), 7.39 (d, 2H), 7.46 (d, 2H), 8.22 (d, 1H); Mass Spectrum (Chemical Ionization, 1% $NH_3$ in $CH_4$) m/z 394 (M+H).

Step 2: Ac-(4-(Difluorophosphonomethyl))-L-Phe-L-Glu-N(methyl)(3-cyclohexylpropyl)

The title compound was synthesized in a manner similar to Example 4 only Ac-[4-(diethoxyphosphonyl)difluoromethyl]-L-Phe was coupled rather than the D/L mixture. The purified peptide (30 mg) was deprotected with 1M trimethysilyl triflate and 2M dimethylsulfide in trifluoroacetic acid (3 mL) for 16 hours at room temperature. Water was added to quench excess trimethysilyl triflate, and the resulting solution was concentrated at reduced pressure to remove volatiles.

The remaining solution was diluted with trifluoroacetic acid and water and purified by preparative HPLC, as previously described, to provide the product as a colorless solid after lyophilization (22 mg). HPLC 100%, rt=16.6 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 603 (M–H).

EXAMPLE 6

[S-(R*,R*)]-4-[(3-Cyclohexyl-propyl)-methyl)-carbamoyl]-4-[2-[(morpholine-4-carbonyl)-amino]-3-(4-phosphonooxy-phenyl)-propionylamino]-butyric acid or 4-Morpholinecarbonyl-(O-phosphono)-L-Tyr-L-Glu-N(methyl)(3-cyclohexylpropyl)

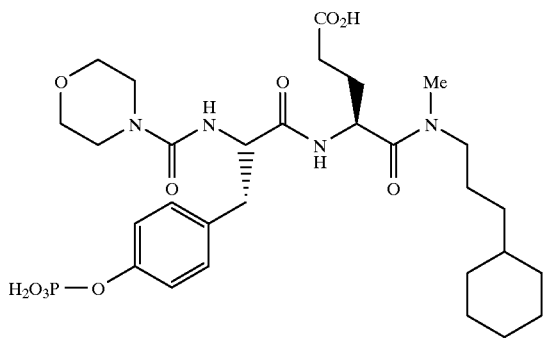
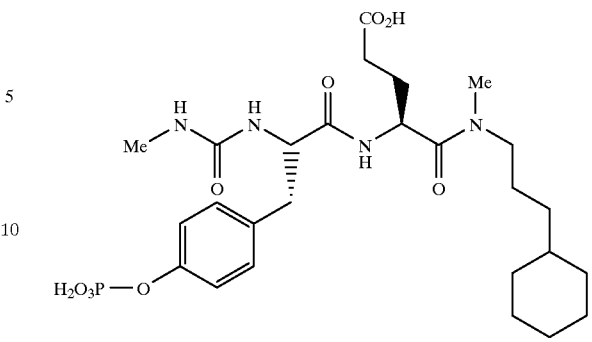

Step 1: 4-Morpholinecarbonyl-L-Tyr(Bzl)-OBzl

To H-Tyr(Bzl)-Obzl-p-tosylate (7.5 mmol, 4.0 g) in dichloromethane (50 mL) at 0° C. was added N-methylpiperidine (7.5 mmol, 0.75 g) followed by dropwise addition of 4-morpholinecarbonyl chloride (7.5 mmol, 1.13 g). After stirring 12 hours at room temperature, the mixture was washed sequentially with 10% sulfuric acid, water, saturated sodium bicarbonate and brine to provide product as an oil (3.81 g, 99%).

Step 2: 4-Morpholinecarbonyl-L-Tyr-OH

A mixture of 4-Morpholinecarbonyl-L-Tyr(Bzl)-OBzl (8.0 mmol, 3.81 g), methanol (50 mL), and 10% palladium on carbon (0.50 g) was stirred under a hydrogen atmosphere for 20 hours. The mixture was filtered over Celite, and the solvent was removed at reduced pressure to give (2.35 g, 97%) of the product as an oil.

Step 3: 4-Morpholinecarbonyl-L-Tyr-L-Glu(OtBu)-N(methyl)(3-cyclohexylpropyl)

To Fmoc-LGlu(OtBu)-N(methyl)(3-cyclohexylpropyl) (2.0 mmol, 1.12 g) in dichloromethane (20 mL) was added piperidine (4 mL). After 20 minutes toluene (20 mL) was added, and the solvent was removed under reduced pressure. Toluene (20 mL) was again added, and the solvent was evaporated. The resulting residue was dissolved in Dimethylformamide (20 mL) and coupled with the 4-Morpholinecarbonyl-L-Tyr-OH (2.0 mmol, 600 mg) in a manner similar to that described for Example 1 to give a solid residue upon work-up. Chromatography of the residue (2:8, tetrahydrofuran/dichloromethane) gave product as a colorless foam (700 mg, 63%).

Step 4: 4-Morpholinecarbonyl-(O-phosphono)-L-Tyr-L-Glu-N(methyl)(3-cyclohexylpropyl)

The reaction was carried out in a manner similar to that described for Example 1 (Step 3). The product was obtained as a white solid (83 mg). HPLC 89%, rt=17.7 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 639.4.

EXAMPLE 7

[S-(R*,R*)]-4-[(3-Cyclohexyl-propyl)-methyl-carbamoyl]-4-[2-(3-methyl-ureido)-3-(4-phosphonooxy-phenyl)-propionylamino]-butyric acid or N-[(Methylamino)carbonyl]-(O-phosphono)-L-Tyr-L-Glu-N(methyl)(3-cyclohexylpropyl)

Step 1: N-[(Methylamino)carbonyl]-L-Tyr(Bzl)-OBzl

To H-Tyr(Bzl)-OBzl-p-tosylate (11.2 mmol, 6.0 g) in tetrahydrofuran (50 mL) at 0° C. was added N-methylpiperidine (3.60 mL) followed by dropwise addition of methyl isocyanate (14.6 mmol, 0.85 g) in tetrahydrofuran (5 mL). After stirring 2 hours at room temperature, the mixture was evaporated to dryness under reduced pressure. Chromatography of the residue (1:4, ethyl acetate:hexane) provided the product as a white foam (4.72 g, 99%).

Step 2: N-[(Methylamino)carbonyl]-L-Tyr-OH

A mixture of N-methylcarbonyl-L-Tyr(Bzl)-OBzl (4.8 mmol, 2.0 g), methanol (50 mL), and 10% palladium on carbon (0.50 g) was stirred under a hydrogen atmosphere for 20 hours. The mixture was filtered over Celite, and the solvent was removed at the reduced pressure to give (1.27 g, 97%) of the product as an oil.

Step 3: N-[(Methylamino)carbonyl]-L-Tyr-L-Glu(OtBu)-N(methyl)(3-cyclohexylpropyl)

To Fmoc-L-Glu(OtBu)-N(methyl)(3-cyclohexylpropyl) (5.3 mmol, 2.98 g) in dichloromethane (20 mL) was added piperidine (4 mL). After 20 minutes toluene (20 mL) was added, and the solvent was removed under reduced pressure. Toluene (20 mL) was again added, and the solvent was evaporated. The resulting residue was dissolved in dimethylformamide (20 mL) and coupled with the N-methylcarbonyl-L-Tyr-OH (5.3 mmol, 1.27 g) in a manner similar to that described for Example 1 to give a solid residue upon work-up. Chromatography of the residue (2:8, tetrahydrofuran/dichloromethane) gave product as a colorless foam (2.0 g, 67%).

Step 4: N-[(Methylamino)carbonyl]-(O-phosphono)-L-Tyr-L-Glu-N(methyl)(3-cyclohexylpropyl)

The reaction was carried out in a manner similar to that described for Example 1 (Step 3). Product was obtained as a white solid (67 mg). HPLC 97%, rt=18.4 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 583.5 (M–H).

EXAMPLE 8

[S-(R*,R*)]-Phosphoric acid mono-[4-(2-acetylamino-2-{1-[(3-cyclohexyl-propyl)-methyl-carbamoyl]-propylcarbamoyl}-ethyl)-phenyl] ester or Ac-(O-phosphono)-L-Tyr-L-Abu-N(methyl)(3-cyclohexylpropyl)

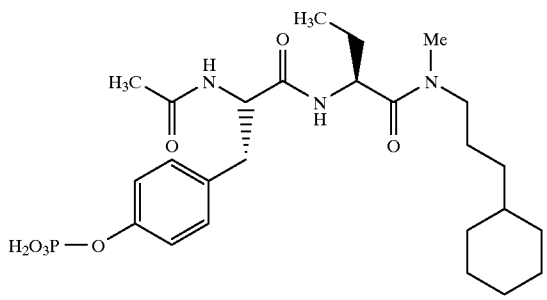

The title compound was synthesized in a manner similar to that described for Example 1. The product was obtained as a colorless solid (78 mg). HPLC 100%, rt=19.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 524.4 (M–H).

EXAMPLE 9

[S-(R*,R*)]-Phosphoric acid mono-[4-(2-acetylamino-2-{1-[(3-cyclohexyl-propyl)-methyl-carbamoyl]-pentylcarbamoyl}-ethyl)-phenyl] ester or Ac-(O-phosphono)-L-Tyr-L-Nle-N(methyl)(3-cyclohexylpropyl)

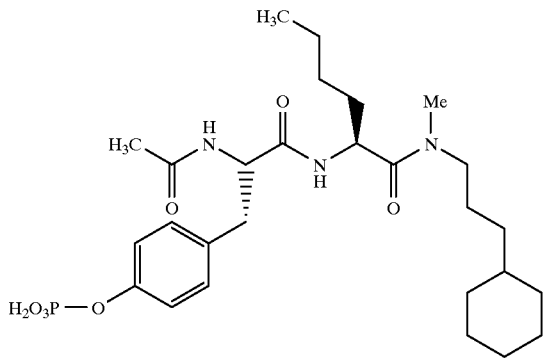

The title compound was synthesized in a manner similar to that described for Example 1. The product was obtained as a colorless solid (92 mg). HPLC 100%, rt=21.5 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 552.4 (M–H).

EXAMPLE 10

[S-(R*,R*)]-{[4-(2-Acetylamino-2-{1-[(3-cyclohexylpropyl)-methyl-carbamoyl]-propylcarbamoyl}-ethyl)-phenyl]-difluoro-methyl}-phosphonic acid or Ac-(4-(difluorophosphonomethyl))-L-Phe-L-Abu-N(methyl) (3-cyclohexylpropyl)

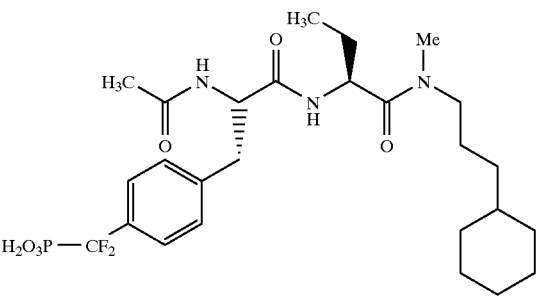

Step 1: Boc-L-Abu-N-(methyl)(3-cyclohexylpropyl)
Boc-L-Abu-N(methyl)(3-cyclohexylpropyl) was synthesized in a manner similar to that described for Example 1 (Step 1) to yield a colorless oil. $^1$H NMR (CDCl$_3$, 400 MHz): δ 0.87 (m, 2H), 0.93 (t, 3H), 1.17 (m, 6H), 1.43 (s, 9H), 1.50–1.80 (m, 7H), 2.92+3.03 (s, 3H, rotational isomers), 3.23–3.44 (m, 2H), 4.54 (m, 1H), 5.40 (2d, 1H, rotational isomers).

Step 2: Ac-(4-(difluorophosphonomethyl))-L-Phe-L-Abu-N(methyl)(3-cyclohexylpropyl)
Ac-(4-(difluorophosphonomethyl))-L-Phe-L-Abu-N-(methyl) (3-cyclohexylpropyl) was synthesized in a manner similar to that in Example 5 (Step 2) only Boc-L-Abu-N-(methyl)(3-cyclohexylpropyl) was used rather than Fmoc-L-Glu-N(methyl)(3-cyclohexylpropyl), and was deprotected with TFA. The purified peptide (80 mg) was deprotected with 1M trimethysilyl triflate and 2M dimethylsulfide in trifluoroacetic acid (5 mL) for 3 hours at 0° C. and 1 hour at room temperature. Water was added to quench excess trimethysilyl triflate, and the resulting solution was concentrated under reduced pressure to remove volatiles. The remaining solution was diluted with trifluoroacetic acid and water and purified by preparative HPLC, as previously described, to provided the product as a colorless solid after lyophilization (51 mg). HPLC 100%, rt=18.0 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 558 (M–H).

EXAMPLE 11

4-[(S)-2-Acetylamino-3-(4-phosphonooxy-phenyl)-(S)-propionylamino]-5-oxo-5-((S)-2-phenethyl-pyrrolidin-1-yl)-pentanoic acid

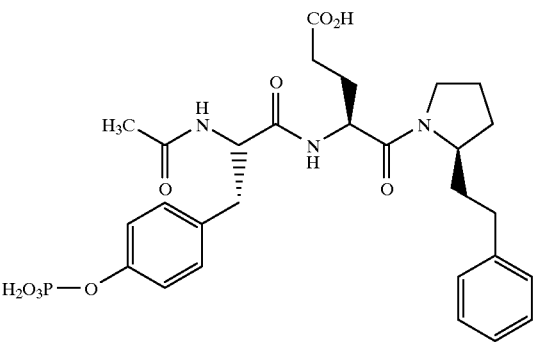

The title compound was synthesized in a manner similar to that described for Example 1. The product was obtained as a colorless solid (51 mg). HPLC 100%, rt=15.7 minutes, C18, eluting with a gradient of 10% to 76% acetonitrile containing 0.1% TFA, and water containing 0.1% TFA over 22 minutes. Electrospray Mass Spectrum (50/50 acetonitrile/water+0.1% ammonium hydroxide) m/z 595.5 (M−H).

EXAMPLE 12

4-[(S)-2-Acetylamino-3-(4-phosphonooxy-phenyl)-(S)-propionylamino]-5-[2-((S)-2-cyclohexyl-ethyl)-pyrrolidin-1-yl]-5-oxo-pentanoic acid

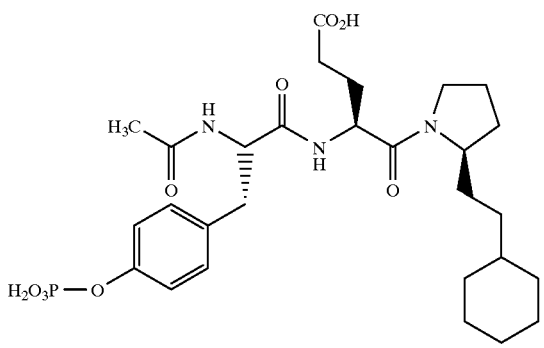

The title compound was synthesized in a manner similar to that described for Example 1. The product was obtained as a colorless solid (51 mg). HPLC 100%, rt=13.3 minutes, C18, eluting with a gradient of 10% to 76% acetonitrile containing 0.1% TFA, and water containing 0.1% TFA over 22 minutes. Electrospray Mass Spectrum (50/50 acetonitrile/water+0.1% ammonium hydroxide) m/z 589.4 (M−H).

EXAMPLE 13

[S-(R*,R*)]-4-[2-Acetylamino-3-(4-phosphonooxy-phenyl)-propionylamino]-4-[2-(5,6,7,8-tetrahydro-naphthalen-1-yl)-ethylcarbamoyl]-butyric acid

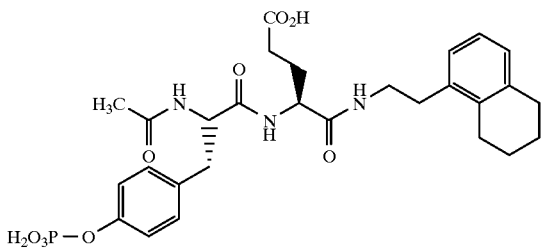

The title compound was synthesized in a manner similar to that described for Example 1. The product was obtained as a colorless solid (178 mg). HPLC 93%, rt=15.6 minutes, C18, eluting with a gradient of 10% to 76% acetonitrile containing 0.1% TFA, and water containing 0.1% TFA over 22 minutes. Electrospray Mass Spectrum (50/50 acetonitrile/water+0.1% ammonium hydroxide) m/z 588.3 (M−H).

EXAMPLE 14

[S-(R*,R*)]-4-[2-Acetylamino-3-(4-phosphonooxy-phenyl)-propionylamino]-4-(3-phenyl-propylcarbamoyl)-butyric acid or Ac-(O-phosphono)L-Tyr-L-Glu-NH(3-phenylpropyl)

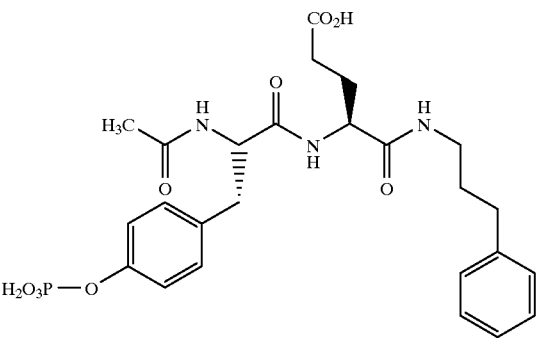

The title compound was synthesized in a manner similar to that described for Example 1. The product was obtained as a colorless powder (52 mg). HPLC 100%, rt=14.0 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 548.3 (M−H).

EXAMPLE 15

[S-(R*,R*)]-4-[2-Acetylamino-3-(4-phosphonooxy-phenyl)-propionylamino]-4-[(naphthalen-1-ylmethyl)-carbamoyl]-butyric acid

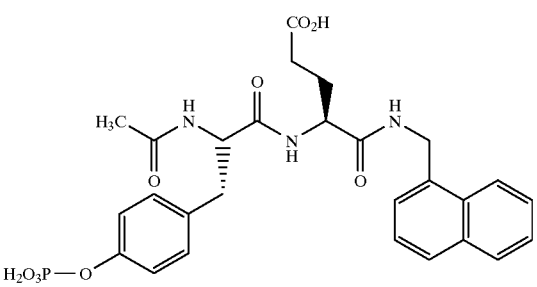

The title compound was synthesized in a manner similar to that described for Example 1. The product was obtained as a colorless powder (35 mg). HPLC 100%, rt=14.6 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 571.5 (M−H).

EXAMPLE 16

[S-(R*,R*)]-4-[2-Acetylamino-3-(4-phosphonooxy-phenyl)-propionylamino]-4-phenethylcarbamoyl-butyric acid or Ac-(O-phosphono)L-Tyr-L-Glu-NH(2-phenylethyl)

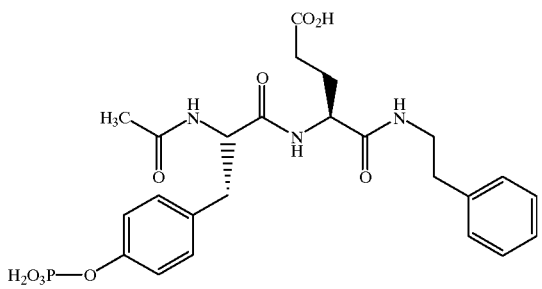

The title compound was synthesized in a manner similar to that described for Example 1. The product was obtained as a colorless powder (27 mg). HPLC 100%, rt=12.5 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 534.5 (M−H).

EXAMPLE 17

4-[(S)-2-Acetylamino-3-(4-phosphonooxy-phenyl)-(S)-propionylamino]-4-[methyl-((S)-1-methyl-2-phenylethyl)-carbamoyl]-butyric acid or Ac-(O-phosphono)-L-Tyr-L-Glu-N(methyl)((S)-1-methyl-2-phenylethyl)

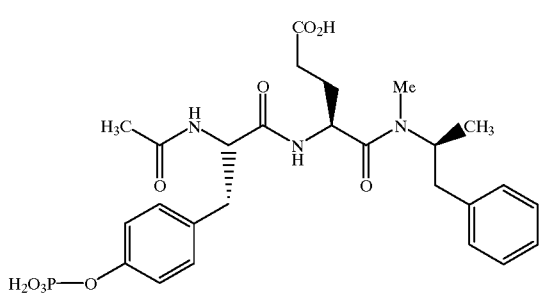

The title compound was synthesized in a manner similar to that described for Example 1. The product was obtained as a colorless solid (176 mg). HPLC 91%, rt=13.8 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 563.4 (M−H).

EXAMPLE 18

4-[(S)-2-Acetylamino-3-(4-phosphonooxy-phenyl)-(S)-propionylamino]-4-((S)-1-methyl-2-phenylethylcarbamoyl)-butyric acid or Ac-(O-phosphono)-L-Tyr-L-Glu-NH((S)-1-methyl-2-phenylethyl)

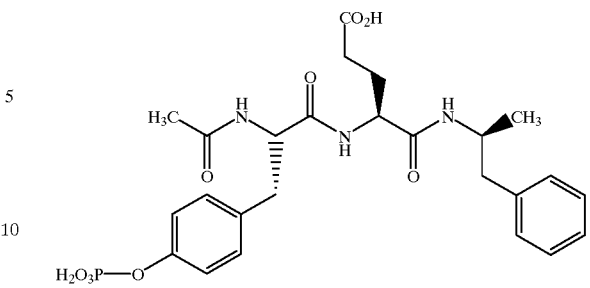

The title compound was synthesized in a manner similar to that described for Example 1. The product was obtained as a colorless solid (251 mg). HPLC 100%, rt=13.6 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 549.4 (M−H).

EXAMPLE 19

[S-(R*,R*)]-4-[2-Acetylamino-3-(4-phosphonooxy-phenyl)-propionylamino]-4-[methyl-(3-phenyl-propyl)-carbamoyl]-butyric acid or Ac-(O-phosphono)-L-Tyr-L-Glu-N(methyl)(3-phenylpropyl)

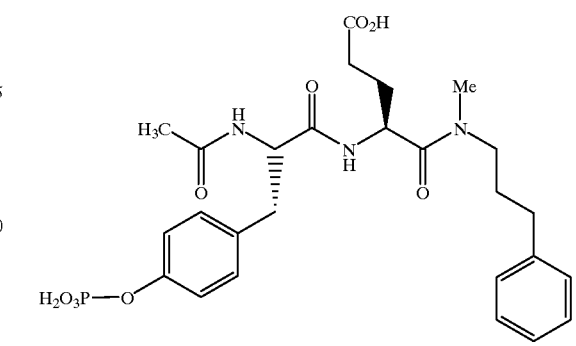

The title compound was synthesized in a manner similar to that described for Example 1. The product was obtained as a colorless solid (108 mg). HPLC 85%, rt=14.5 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 562.5 (M−H).

EXAMPLE 20

[S-(R*,R*)]-Phosphoric acid mono-(4-{2-acetylamino-2-[2-(4-hydroxy-phenyl)-1-(3-phenyl-propylcarbamoyl)-ethyl-carbamoyl]-ethyl}-phenyl) ester

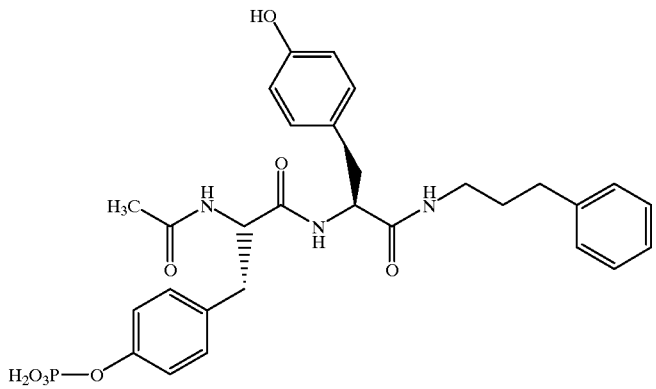

The title compound was synthesized in a manner similar to that described for Example 1. The product was obtained as a colorless powder (110 mg). HPLC 100%, rt=15.6 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 584.3 (M–H).

EXAMPLE 21

[S-(R*,R*)]4-[2-Acetylamino-3-(4-phosphonooxy-phenyl)-propionylamino]-4-[2-(2-methoxy-phenyl)-ethylcarbamoyl]-butyric acid or Ac-(O-phosphono)-L-Tyr-L-Glu-NH[2-(2-methoxyphenyl)-ethyl]

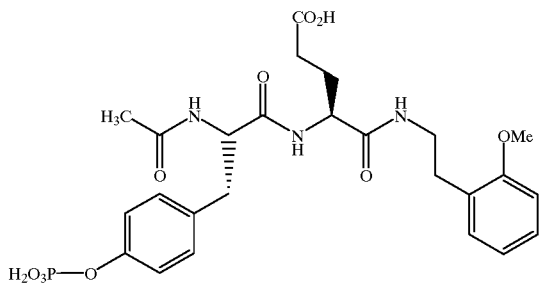

The title compound was synthesized in a manner similar to that described for Example 1. The product was obtained as a colorless powder (62 mg). HPLC 98%, rt=14.6 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 579.4 (M–H).

EXAMPLE 22

[S-(R*,R*)]-4-[2-Acetylamino-3-(4-phosphonooxy-phenyl)-propionylamino]-4-(2-p-tolyl-ethylcarbamoyl)-butyric acid or Ac-(O-phosphono)-L-Tyr-L-Glu-NH[2-(4-methylphenyl)-ethyl]

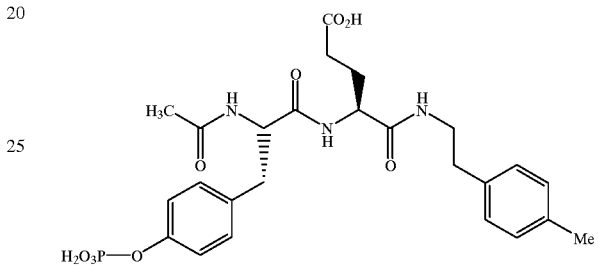

The title compound was synthesized in a manner similar to that described for Example 1. The product was obtained as a colorless powder (109 mg). HPLC 92%, rt=13.7 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 548.4 (M–H).

EXAMPLE 23

[S-(R*,R*)]-4-[2-Acetylamino-3-(4-phosphonooxy-phenyl)-propionylamino]-4-{[2-(2-methoxy-phenyl)-ethyl]-methyl-carbamoyl}-butyric acid or Ac-(O-phosphono)-L-Tyr-L-Glu-N(methyl)[2-(2-methoxyphenyl)-ethyl]

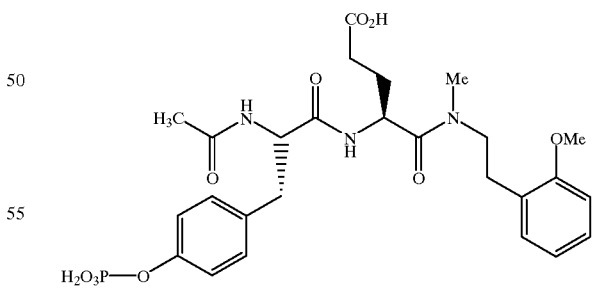

Step 1: N-(t-Butyloxycarbonyl)-2-(2-methoxyphenyl)-ethylamine

To 2-methoxyphenylethylamine (163 mmol, 24 g) in tetrahydrofuran (150 mL) at 0° C. was added triethylamine (180 mmol, 25 mL) followed by dropwise addition of di-t-butyloxycarbonyl dicarbonate (180 mmol, 39.15 g) in 75 mL of tetrahydrofuran. After 12 hours, the solvent was evaporated. The resulting residue was dissolved in ethyl acetate (150 mL), washed with 10% sulfuric acid, then saturated sodium bicarbonate to provide the product as white solid (45 g, 99%).

Step 2: N-methyl-2-(2-methoxyphenyl)-ethylamine

To N-(t-Butyloxycarbonyl)-2-(2-methoxyphenyl)-ethylamine (182.7 mmol, 45.9 g) in dry tetrahydrofuran (200 mL) at 0° C. was added, in portions, lithium aluminum hydride (219.2 mmol, 8.3 g) under $N_2$. After stirring at 0° C. for 1 hour, the ice-bath was removed and then the reaction heated to reflux for 24 hours, cooled to room temperature then to 0° C.; the excess lithium aluminum hydride was destroyed very carefully with 20% potassium hydroxide solution (1.3 equivalent). After removing the salt by filtration, the filtrate was dried then evaporated to dryness to give product as a white solid (26.2 g, 87%).

Step 3: Fmoc-L-Glu(OtBu)-N(methyl)[2-(2-methoxyphenyl)-ethyl]

The compound was synthesized in a manner similar to that described for Example 1 (first step).

Step 4: Ac-L-Tyr-L-Glu(OtBu)-N(methyl)[2-(2-methoxyphenyl)-ethyl]

The compound was synthesized in a manner similar to that described for Example 1 (second step).

Step 5: Ac-(O-phosphono)-L-Tyr-L-Glu-N(methyl)[2-(2-methoxyphenyl)-ethyl]

The title compound was synthesized in a manner similar to that described for Example 1. The product was obtained as a white solid (400 mg). HPLC 100%, rt=13.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 578.4 (M–H).

EXAMPLE 24

[S-(R*,R*)]-4-[2-Acetylamino-3-(4-phosphonooxyphenyl)-propionylamino]-4-[3-(3-carbamoylmethoxyphenyl)-propylcarbamoyl]-butyric acid or Ac-(O-phosphono)-L-Tyr-L-Glu-NH{3-[3-(O-acetamido)-phenyl]propyl}

Step 2: 3-[3-(O-acetamido)-phenyl]-propyl alcohol

To 3-(3-hydroxyphenyl)-propyl alcohol (10.73 mmol, 1.63 g) in acetone (75 mL) was added 2-bromoacetamide (11.80 mmol, 1.62 g) and potassium carbonate (11.80 mmol, 1.63 g). The reaction mixture was heated to reflux for 48 hours, cooled to room temperature, filtered, then the filtrate was concentrated to give product as white solid (2.20 g, 98%).

Step 3: 3-[3-(O-acetamido)-phenyl]-propyl-(O-methanesulfonyl)

To 3-[3-(O-acetamido)-phenyl]-propyl alcohol (11.80 mmol, 2.20 g) in dichloromethane (50 mL) at –10° C. (ice/methanol) was added triethylamine (17.70 mmol, 2.5 mL), then dropwise addition of methanesulfonyl chloride (12.40 mmol, 1 mL). After stirring at –10° C. for 1 hour, the reaction mixture was washed with water, 10% $H_2SO_4$, saturated sodium bicarbonate, dried ($MgSO_4$), filtered, and concentrated to give product as an oil (2.98 g, 88%).

Step 4: 3-[3-(O-acetamido)-phenyl]-propyl azide

To 3-[3-(O-acetamido)-phenyl]-propyl-(O-methanesulfonyl) (10.40 mmol, 2.98 g) in dimethylformamide (30 mL) was added sodium azide (13.6 mmol, 0.90 g). After stirring at room temperature for 48 hours, the reaction mixture was quenched using water, then extracted with ether (4×100 mL), washed with saturated sodium bicarbonate, dried ($MgSO_4$), filtered, then concentrated to give product as colorless oil (1.90 g, 78%).

Step 5: 3-[3-(O-acetamido)-phenyl]-propyl amine

3-[3-(O-acetamido)-phenyl]-propyl azide (8.10 mmol, 1.90 g) was catalytically reduced using 5% palladium on carbon (0.50 g) in tetrahydrofuran (75 mL). Hydrogenation was carried out on a Parr apparatus for 15 hours at 50 psi $H_2$. After filtration. the solvent was removed under reduced pressure. The product was obtained as a white solid (1.28 g, 75%).

Step 6: Fmoc-L-Glu(OtBu)-NH{3-[3-(O-acetamido)-phenyl]-propyl}

This compound was synthesized in a manner similar to that described for Example 1 (Step 1).

Step 7: Ac-L-Tyr-L-Glu(OtBu)-NH{3-[3-(O-acetamido)-phenyl]propyl}

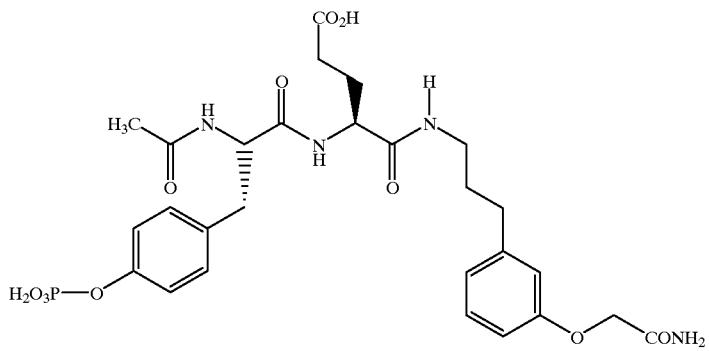

Step 1: 3-(3-Hydroxyphenyl)-propyl alcohol

To 3-(3-hydroxyphenyl)-propionic acid (60.2 mmol, 10.0 g) in dry tetrahydrofuran (200 mL) at 0° C. was added, in portions, lithium aluminum hydride (72.2 mmol, 2.74 g) under $N_2$. After stirring at 0° C. for 1 hour, the ice-bath was removed and then the reaction heated to reflux for 24 hours, cooled to room temperature then to 0° C.; the excess lithium aluminum hydride was destroyed very carefully with 20% potassium hydroxide solution (1.3 equivalent). After removing the salt by filtration, the filtrate was dried then evaporated to dryness to give product as a white solid (7.2 g, 78%).

This compound was synthesized in a manner similar to that described for Example 1 (Step 2).

Step 8: Ac-(O-phosphono)-L-Tyr-L-Glu-NH{3-[3-(O-acetamido)-phenyl]propyl}

The title compound was synthesized in a manner similar to that described for Example 1. The product was obtained as a white solid (70 mg). HPLC 93%, rt=12.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 622.4 (M–H).

EXAMPLE 25

[S-(R*,R*)]-4-[{2-[2-Acetylamino-3-(4-phosphonooxyphenyl)-propionylamino}-propionyl]-(3-cyclohexylpropyl)-amino]-butyric acid or Ac-(O-phosphono)-L-Tyr-L-Ala-N(3-carboxypropyl)(3-cyclohexylpropyl)

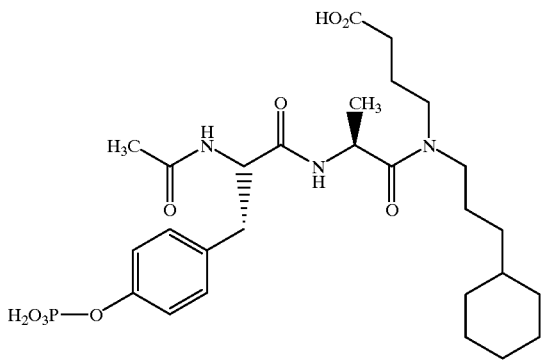

The title compound was synthesized in a manner similar to that described for Example 1. The product was obtained as a colorless powder (51 mg). HPLC 100%, room temperature 19.9 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 582.3 (M–H).

EXAMPLE 26

[S-(R*,R*)]-4-[{2-[2-Acetylamino-3-(4-phosphonooxyphenyl)-propionylamino}-propionyl]-(3-phenyl-propyl)-amino]-butyric acid or Ac-(O-phosphono)-L-Tyr-L-Ala-N(3-carboxypropyl) (3-phenylpropyl)

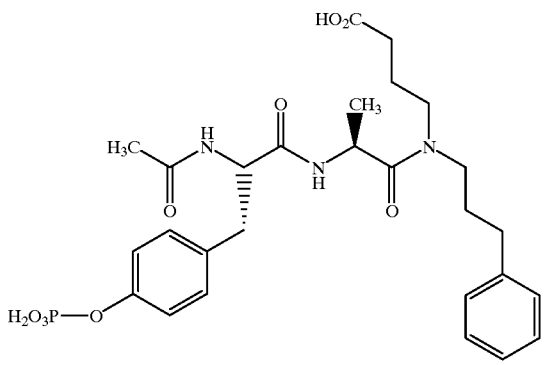

Step 1: Aminobutanoate-gamma-tert-butyl ester

Aminobutanoate-gamma-tert-butyl ester can be prepared in accordance with methods well known to those skilled in the art. (See, for example, Sluka, et al., *J. Amer. Chem. Soc.*, 1990;112:6369–6374.)

Step 2: 4-(3-Phenyl-propylamino)-butyric acid tert-butyl ester

To a solution of aminobutanoate-gamma-tert-butyl ester in N,N-dimethylformamide (500 mL) at room temperature was added triethylamine (28 mL, 210.2 mmol), followed by dropwise addition of 1-bromo-3-phenylpropane (15.2 mL, 100.6 mmol). The reaction was stirred overnight at room temperature then concentrated under reduced pressure to 20 mL. The residue was then diluted with ethyl acetate and washed with saturated sodium chloride (3×250 mL), dried over magnesium sulfate, filtered, and concentrated under reduced pressure to yield a white powder. The powder was dried under reduced pressure to yield (27.0 g, 99%). $^1$H NMR (400 MHz, DMSO): δ 9.00 (bs, 1H), 7.30 (m, 2H), 7.21 (m, 3H), 2.86 (m, 4H), 2.65 (t, 2H), 2.32 (t, 2H), 1.94 (dt, 2H), 1.85 (dt, 2H), 1.40 (s, 9H); Mass Spectrum (Chemical Ionization, 1% NH$_3$ in CH$_4$) m/z 278 (M+H).

Step 3: Ac-(O-phosphono)-L-Tyr-L-Ala-N(3-propylcarboxy)(3-phenylpropyl)

The title compound was synthesized in a manner similar to that described for Example 1. The product was obtained as a colorless powder (127 mg). HPLC 100%, rt=15.1 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 576.7 (M–H).

EXAMPLE 27

[S-(R*,R*)]-5-[{2-[2-Acetylamino-3-(4-phosphonooxyphenyl)-propionylamino]-propionyl}-(3-phenyl-propyl)-amino]-pentanoic acid or Ac-(O-phosphono)-L-Tyr-L-Ala-N(4-carboxybutyl) (3-phenylpropyl)

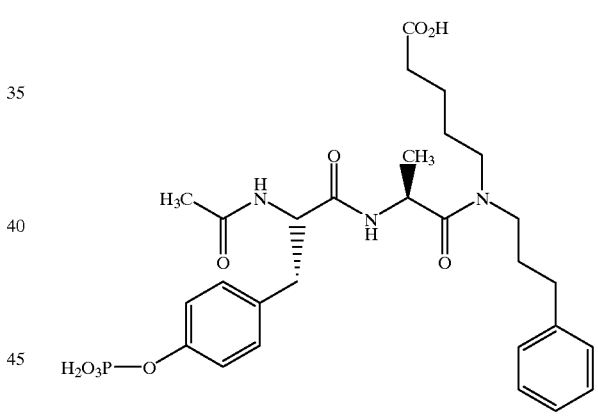

The title compound was synthesized in a manner similar to that described for Example 1. The product was obtained as a colorless powder (76 mg). HPLC 100%, rt=16.1 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 590.3 (M–H).

EXAMPLE 28

[S-(R*,R*)]-Phosphoric acid mono-[4-(2-acetylamino-2-{1-[butyl-(3-phenyl-propyl)-carbamoyl]-ethylcarbamoyl}-ethyl)-phenyl] ester

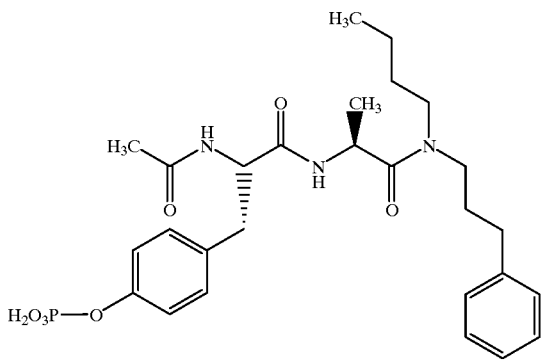

The title compound was synthesized in a manner similar to that described for Example 1. The product was obtained as a colorless powder (59 mg). HPLC 100%, rt=18.5 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 547.4 (M–H).

EXAMPLE 29

[S-(R*,R*)]-4-[2-Acetylamino-3-(4-phosphonooxy-phenyl)-propionylamino]-4-[3-(4-carboxymethoxy-phenyl)-propylcarbamoyl]-butyric acid or Ac-(O-phosphono)-L-Tyr-L-Glu-NH{3-[4-(O-acetic acid)-phenyl]propyl}

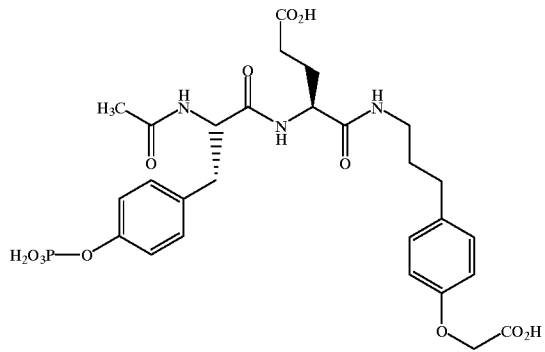

The title compound was synthesized in a manner similar to that described for Example 1. The product was obtained as a white solid (60 mg). HPLC 93%, rt=12.7 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 623.4 (M–H).

EXAMPLE 30

4-[(S)-2-Acetylamino-3-(4-phosphonooxy-phenyl)-(S)-[propionylamino]-5-((S)-2-benzyl-pyrrolidin-1-yl)-5-oxo-pentanoic acid or Ac-(O-phosphono)-L-Tyr-L-Glu-L-Pro(2-decarboxy-2-benzyl)

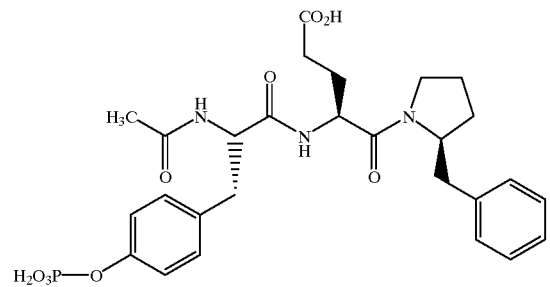

The title compound was synthesized in a manner similar to that described for Example 1. The product was obtained as a colorless solid (167 mg). HPLC 100%, rt=15.4 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 575.5 (M–H).

EXAMPLE 31

L-Tyrosinamide, N-acetyl-O-phosphono-L-tyrosyl-N-(3-phenylpropyl)-O-phosphono- or Ac-(O-phosphono)-L-Tyr-(O-phosphono)-L-Tyr-NH(3-phenylpropyl)

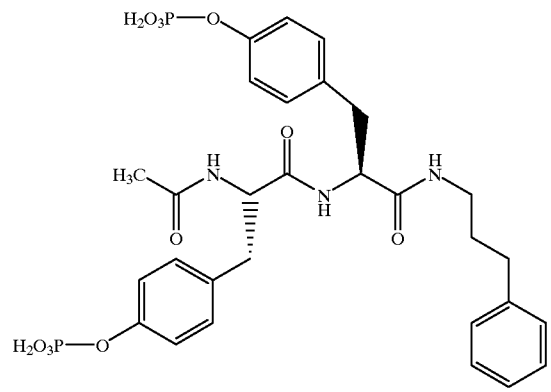

The title compound was synthesized in a manner similar to that described for Example 1. The product was obtained as a colorless solid (64 mg). HPLC 96%, rt=14.5 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 663.3 (M–H).

EXAMPLE 32

4-[(RS)-2-(Acetyl-methyl-amino)-3-(4-phosphonooxy-phenyl)-(S)-propionylamino]-4-(3-phenylpropylcarbamoyl)-butyric acid or Ac-(N-methyl)(O-phosphono)-D/L-Tyr-L-Glu-NH(3-phenylpropyl)

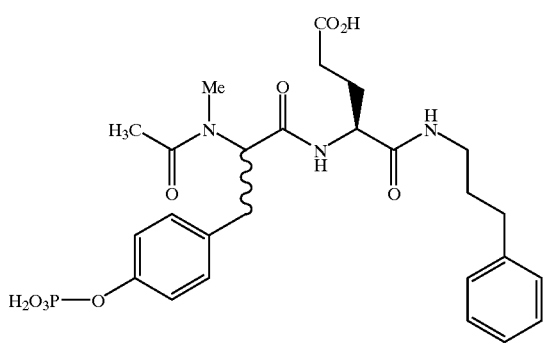

The title compound was synthesized in a manner similar to that described for Example 1. The product was obtained as a colorless solid (52 mg). HPLC 100%, rt=14.9 and 15.13 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 563.6 (M−H).

EXAMPLE 33

[S-(R*,R*)]-4-[2-Methanesulfonylamino-3-(4-phosphonooxy-phenyl)-propionylamino]-4-(3-phenyl-propylcarbamoyl)-butyric acid or Methylsulfonyl-(O-phosphono)-L-Tyr-L-Glu-NH(3-phenylpropyl)

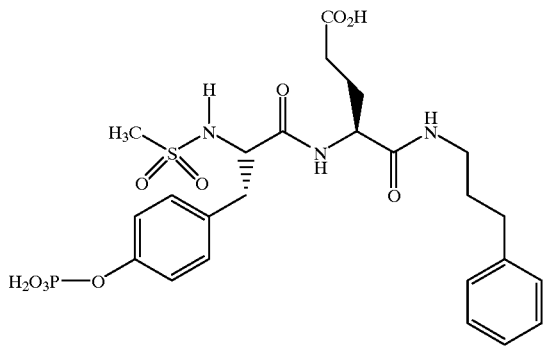

The title compound was synthesized in a manner similar to that described for Example 1. The product was obtained as a colorless powder (71 mg). HPLC 83%, rt=15.6 minutes, C18 column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 584.3 (M−H).

EXAMPLE 34

[S-(R*,R*)]-[4-(2-Acetylamino-2-{1-[(3-cyclohexylpropyl)-methyl-carbamoyl]-propylcarbamoyl}-ethyl)-phenyl]-phosphonic acid or Ac-(4-phosphonyl)-L-Phe-L-Abu-N(methyl)(3-cyclohexylpropyl)

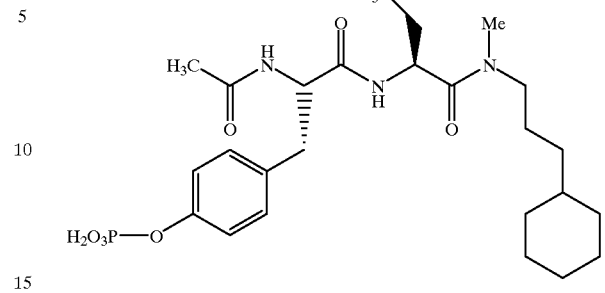

Step 1: Ac-[4-(diethoxyphosphonyl)]-L-Phe

Ac-[4-(diethoxyphosphonyl)]-L-Phe was prepared in a manner similar to Ac-[4-(diethoxyphosphonyl)-difluoromethyl]-L-Phe, except starting from Boc-[4-(diethoxyphosphonyl)-difluoromethyl]-L-Phe Benzyl ester, which can prepared in accordance with methods well known to those skilled in the art. (See, for example, Thurieau, et al., *J. Med. Chem.*, 1994;37:625–629.) (See Example 5, Step 1.) Deprotection, acetylation, and hydrogenation yielded a solid foam. $^1$H NMR (DMSO, 400 MHz): δ 1.22 (t, 6H), 1.77 (s, 3H), 2.91 (dd, 1H), 3.10 (dd, 1H), 3.33 (m, 4H), 4.44 (m, 1H), 7.38 (dd, 2H), 7.61 (dd, 2H), 8.22 (d, 1H); Electrospray Mass Spectrum (50/50 acetonitrile/water+0.1% ammonium hydroxide) m/z 342 (M−H).

Step 2: Ac-(4-phosphonyl)-L-Phe-L-Abu-N(methyl)(3-cyclohexylpropyl)

The title compound was synthesized in a manner similar to Example 10 except Ac-[4-(phosphonyl)-difluoromethyl]-L-Phe was coupled in rather than Ac-[4-(diethoxyphosphonyl)difluoromethyl]-L-Phe. The purified peptide (30 mg) was deprotected with trimethysilyl bromide (1 mL) in dichloromethane (2 mL) for 4 hours at room temperature. Water (1 mL) and trifluoroacetic acid (1 mL) were added to quench excess trimethysilyl bromide, and the resulting solution was concentrated at reduced pressure to remove volatiles. An additional 1 mL of TFA was added, and the mixture was concentrated to −200 µL and then precipitated with diethyl ether. The resulting solid was filtered, washed with diethyl ether, and dried under vacuum overnight to yield 27 mg of an off-white solid. HPLC 98%, rt=18.6 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 508 (M−H).

EXAMPLE 35

(S)-4-[3-carboxymethyl-3-(4-phosphonooxy-benzyl)-ureido]-4-[(3-cyclohexyl-propyl)-methyl-carbamoyl]-butyric acid

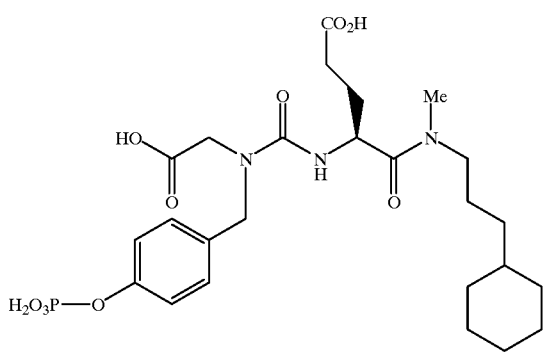

To Glu(OtBu)-N(Me)-3-cyclohexylpropyl (360 mg, 1.0 mmol) synthesized as an intermediate in Example 1, ice, dichloromethane (20 mL), and saturated sodium bicarbonate (20 mL) in a separatory funnel was added phosgene in toluene (7.5 equiv.). The mixture was shaken for 5 minutes, then the organic layer was separated, dried over magnesium sulfate, and concentrated to give the isocyanate as a colorless oil. The isocyanate was treated in dichloromethane (20 mL) with 4-hydroxybenzyl glycine-t-butyl ester (250 mg, 1.0 mmol) and triethylamine (0.15 mL, 1.0 mmol) for 1 hour. Ethyl acetate was added, and the reaction mixture was washed with 10% sulfuric acid, then water, and then brine. After drying over magnesium sulfate, the solvent was removed under reduced pressure to give then urea as a colorless oil (500 mg, 83%). The crude urea was phosphorylated, oxidized, deprotected, and purified in a manner similar to Example 1, giving the title compound (49 mg) as a colorless solid. HPLC 100%, rt=17.4 minutes, C18, eluting with a gradient of 0% to 66% acetonitrile containing 0.1% TFA, and water containing 0.1% TFA over 22 minutes. Electrospray Mass Spectrum (50/50 acetonitrile/water+ 0.1% ammonium hydroxide) m/z 552.4 (M–H).

EXAMPLE 36
(S)-4-[(3-Cyclohexyl-propyl)-methyl-carbamoyl]-4-[3-(6-phosphonoxy-naphthalen-1-yl)-ureido]-butyric acid

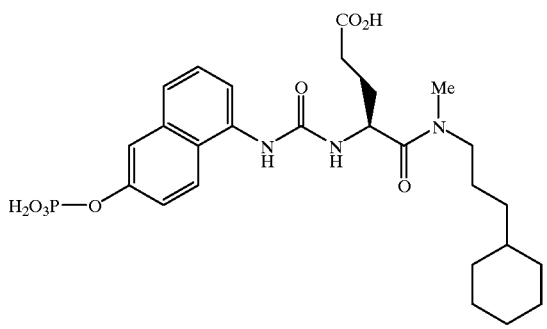

Step 1: (S)-2-[3-(6-Hydroxy-naphthalen-1-yl)-ureido]-pentanedioic acid 5-tert-butyl ester 1-methyl ester To H-Glu(OtBu)-OCH₃ (2.0 mmol, 0.50 g) in dichloromethane (25 mL) at 0° C. was added pyridine (8 mmol, 0.66 mL) then followed by dropwise addition of phosgene in toluene (3.0 mmol, 1.60 mL, 1.92 M). After stirring at 0° C. for 2 hours, 1-amino-6-naphthol (2.0 mmol, 0.32 g) was added in dichloromethane. After stirring at room temperature for 12 hours, the reaction mixture was evaporated to dryness and purified on silica gel (1:19, methanol/dichloromethane) to provide product as a light brown solid (0.71 g, 88%).

Step 2: (S)-2-[3-(6-Hydroxy-naphthalen-1-yl)-ureido]-pentanedioic acid 5-tert-butyl ester To the methyl ester from Step 1 above (5 mmol, 2.0 g) was added potassium hydroxide (5 mmol, 0.28 g) in water (7 mL), and heated at 50° C. After stirring for 36 hours, the reaction mixture was evaporated to dryness, the residue was dissolved in water (15 mL), acidified to pH≈5 using 0.50 N hydrochloric acid, extracted with the ethyl acetate (4×50 mL), and dried to provide product as a light brown oil (1.20 g, 62%).

Step 3: (S)-4-[(3-Cyclohexyl-propyl)-methyl-carbamoyl]-4-[3-(6-hydroxy-naphthalen-1-yl)-ureido]-butyric acid tert-butyl ester This step was synthesized in a manner similar to that described for Example 1 (Step 1).

Step 4: (S)-4-[(3-Cyclohexyl-propyl)-methyl-carbamoyl]-4-[3-(6-phosphonoxy-naphthalen-1-yl) ureidol-butyric acid The title compound was synthesized in a manner similar to that described for Example 1. Product was obtained as a white solid (27 mg). HPLC 100%, rt=18.9 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 549.4 (M–H).

EXAMPLE 37

[S -(R*,R*)]-4-[2-Acetylamino-3-(4-phosphonooxy-phenyl)-propionylamino]-4-(5-methyl-hexylcarbamoyl)-butyric acid or Ac-(O-phosphono)-L-Tyr-L-Glu-N(5-methylhexyl)

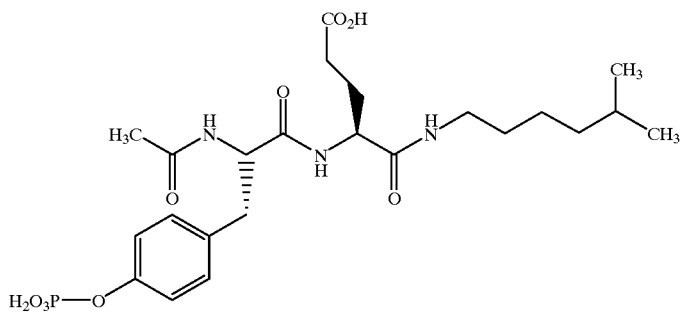

The title compound was synthesized in a manner similar to that described for Example 1. The product was obtained as a colorless solid (154 mg). HPLC 95%, rt=15.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 529.6 (M–H).

EXAMPLE 38

[S-(R*,R*)]-4-[2-Acetylamino-3-(4-phosphonooxy-phenyl)-propionylamino]-4-(4-methyl-hexylcarbamoyl)-butyric acid or
Ac-(O-phosphono)-L-Tyr-L-Glu-NH((R,S)-4-methylhexyl)

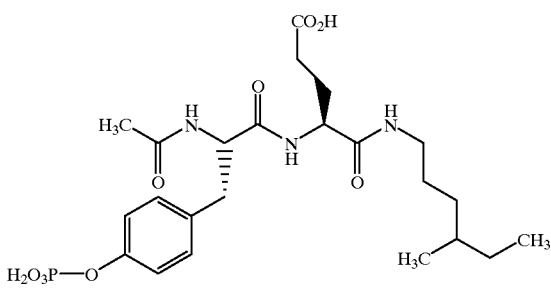

The title compound was synthesized in a manner similar to that described for Example 1. The product was obtained as a colorless solid (91 mg). HPLC 94%, rt=15.1 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 528.5 (M–H).

EXAMPLE 39

Phosphoric acid mono-[4-(4-benzyloxy-3-carbamoyl-benzylcarbamoyl)-phenyl] ester

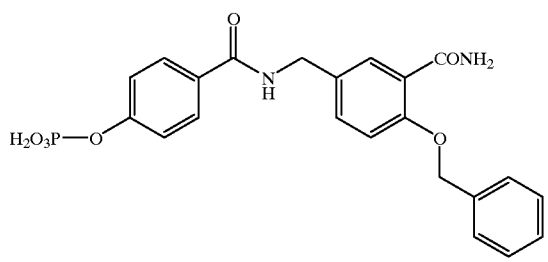

The title compound was synthesized in a manner similar to that described for Example 44. The product was obtained as a colorless powder (21 mg). HPLC 100%, rt=14.8 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 455.2 (M–H).

EXAMPLE 40

Phosphoric acid mono-{4-[3-carbamoyl-4-(3-methyl-benzyloxy)-benzylcarbamoyl]-phenyl} ester

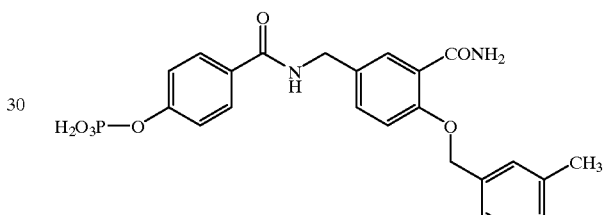

The title compound was synthesized in a manner similar to that described for Example 44. The product was obtained as a colorless powder (73 mg). HPLC 100%, rt=16.9 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 469.3 (M–H).

EXAMPLE 41

Phosphoric acid mono-{4-[3-carbamoyl-4-(3,5-dimethyl-benzyloxy)-benzylcarbamoyl]-phenyl} ester

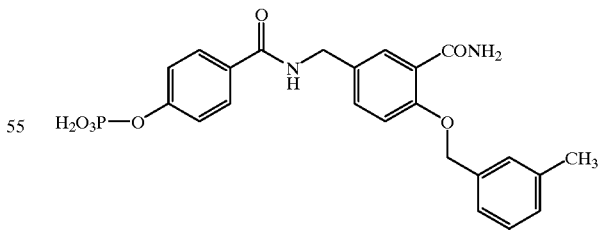

The title compound was synthesized in a manner similar to that described for Example 44. The product was obtained as a colorless powder (85 mg). HPLC 100%, rt=17.2 minutes, C18, column eluting with a gradient of 0% to 66% acetonitrile containing 0.1% TFA and water containing 0.1%

TFA over 22 minutes. Electrospray Mass Spectrum (50/50 acetonitrile/water+0.1% ammonium hydroxide) m/z 483.4 (M–H).

EXAMPLE 42

Phosphoric acid mono-{4-[3-carbamoyl-4-(4-methyl-pentyloxy)-benzylcarbamoyl]-phenyl} ester

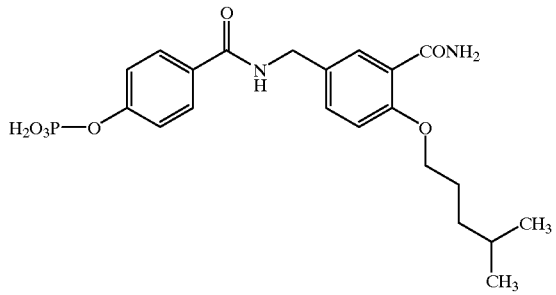

The title compound was synthesized in a manner similar to that described for Example 44. The product was obtained as a colorless powder (8 mg). HPLC 100%, rt=18.7 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 449.4 (M–H).

EXAMPLE 43

Phosphoric acid mono-{4-[3-carbamoyl-4-(4-methyl-hexyloxy) -benzylcarbamoyl]-phenyl} ester

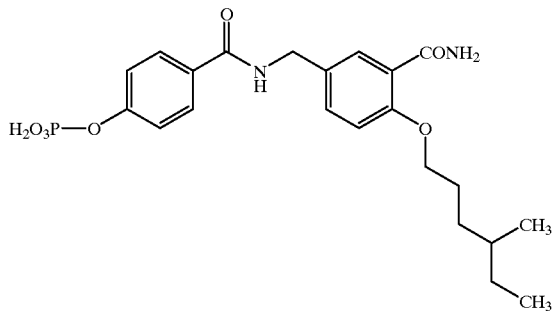

The title compound was synthesized in a manner similar to that described for Example 44. The product was obtained as a colorless powder (100 mg). HPLC 99%, rt=18.3 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 463.4 (M–H).

EXAMPLE 44

Phosphoric acid mono-[4-(3-carbamoyl-4-cyclohexyl-methoxy-benzylcarbamoyl)-phenyl] ester

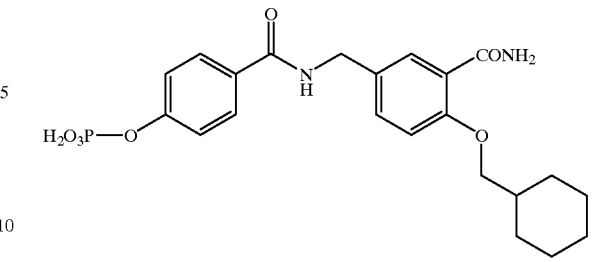

Step 1: 5-Aminomethylsalicylic acid

5-Aminomethylsalicylic acid can prepared in accordance with methods well known to those skilled in the art. (See, for example, Sekiya, et al., *Chem. Pharm. Bull.*, 1963;11:551–553.)

Step 2: 5-(tert-Butoxycarbonylamino-methyl)-2-hydroxy-benzoic acid

To a solution of 5-aminomethylsalicyclic acid (8.3 g, 49.7 mmol) in 100 mL water and 100 mL of dioxane at 0° C. was added 1N sodium hydroxide (54.7 mL, 54.7 mmol) followed by di-tert-butyl dicarbonate (11.9 g, 54.7 mmol). The reaction was allowed to warm slowly to room temperature and stirred overnight. The reaction was then concentrated under reduced pressure to 15 mL. A layer of ethyl acetate was then added, and the reaction was acidified to pH 2 with saturated potassium hydrogen sulfate. The aqueous layer was then extracted with ethyl acetate (3×150 mL). The combined ethyl acetate layers were combined and washed with saturated sodium chloride (1×150 mL), dried over magnesium sulfate, filtered, and concentrated under reduced pressure to yield a white powder. The powder was collected and washed with ether, followed by drying under reduced pressure to yield (11.5 g, 87%). $^1$H NMR (400 MHz, DMSO): δ 7.67 (s, 1H), 7.38 (d, 2H), 6.91 (d, 1H), 4.04 (d, 2H), 1.41 (s, 9H). Mass Spectrum (Chemical Ionization, 1% $NH_3$ in $CH_4$) m/z 268 (M+H).

Step 3: (3-Carbamoyl-4-hydroxy-benzyl)-carbamic acid tert-butyl ester

To a solution of 5-(tert-Butoxycarbonylamino-methyl)-2-hydroxy-benzoic acid (20.0 g, 74.9 mmol) in 700 mL tetrahydrofuran at 0° C. was added 4-methyl morpholine (12.3 mL, 112.3 mmol), 1-hydroxybenzo-triazole (15.2 g, 112.3 mmol), followed by 1-(3-dimethylaminopropyl)-3-ethylcarbodiimide hydrochloride (21.5 g, 112.3 mmol). Stir for 1 hour at 0° C., then added concentrated ammonium hydroxide (15.2 mL, 112.3 mmol). The reaction was allowed to warm slowly to room temperature and stirred overnight. The reaction was then diluted with ethyl acetate and washed with 5% citric acid (3×250 mL), saturated sodium bicarbonate (3×250 mL), and saturated sodium chloride (1×250 mL), dried over magnesium sulfate, filtered, and concentrated under reduced pressure to yield a pale yellow powder. The powder was collected and washed with ether, followed by drying under reduced pressure to yield (14.0 g, 71%). $^1$H NMR (400 MHz, DMSO): δ 12.77 (bs, 1H), 8.33 (bs, 1H), 7.72 (d, 1H), 7.28 (d, 2H), 6.84 (d, 1H), 4.05 (d, 2H), 1.38 (s, 9H); Mass Spectrum (Chemical Ionization, 1% $NH_3$ in $CH_4$) m/z 267 (M+H).

Step 4: (3-Carbamoyl-4-cyclohexylmethoxy-benzyl)-carbamic acid tert-butyl ester

To a solution of (3-Carbamoyl-4-hydroxy-benzyl)-carbamic acid tert-butyl ester (2.0 g, 7.5 mmol) in 15 mL methanol at room temperature was added cesium carbonate (2.7 g, 8.3 mmol). The reaction was stirred overnight. The reaction was then concentrated under reduced pressure.

N,N-dimethylformamide (50 mL) was then added, and the reaction was then reconcentrated under reduced pressure to remove any remaining methanol. The residue was then suspended in N,N-dimethylformamide (15 mL) and cyclohexylmethyl bromide (1.1 mL, 8.3 mmol) was then added, and the reaction was heated at 65° C. for 4 hours. The reaction was then concentrated under reduced pressure. The residue was diluted with ethyl acetate and 5% citric acid. The organic layer was washed with 5% citric acid (2×50 mL), 1N sodium hydroxide (2×50 mL), 5% citric acid (2×50 mL), and saturated sodium chloride (1×50 mL), dried over magnesium sulfate, filtered, and concentrated under reduced pressure to yield a pale yellow powder. The powder was collected and washed with ether, followed by drying under reduced pressure to yield (1.5 g, 57%). $^1$H NMR (400 MHz, DMSO): δ 7.68 (bs, 1H), 7.52 (d, 2H), 7.36 (t, 1H), 7.27 (d, 2H), 7.05 (d, 1H), 4.04 (d, 2H), 3.88 (d, 2H), 1.76–1.61 (m, 6H), 1.36 (s, 9H), 1.28–1.02 (m, 5H); Mass Spectrum (Chemical Ionization, 1% $NH_3$ in $CH_4$) m/z 363 (M+H).

Step 5: Benzamide 2- (cyclohexylmethoxy)-5-[[[(4-hydroxyphenyl)-carbonyl]amino]-methyl]

A solution of 4N hydrochloric acid in dioxane was added to (3-Carbamoyl-4-cyclohexylmethoxy-benzyl)-carbamic acid tert-butyl ester (1.0 g, 2.7 mmol). The reaction is stirred for 1 hour and then concentrated under reduced pressure to yield a solid. This solid of the amine hydrochloride was then used for the coupling. The above amine hydrochloride was dissolved in N,N-dimethylformamide (30 mL), and the solution was cooled to 0° C. 4-methyl morpholine (0.75 mL, 6.9 mmol) was then added, followed by 1-hydroxybenzotriazole (559 mg, 4.1 mmol), 4-hydroxybenzoic acid (457 mg, 3.3 mmol), and 1-(3-dimethylaminopropyl)-3-ethylcarbodiimide hydrochloride (793 mg, 4.1 mmol). The reaction was allowed to warm slowly to room temperature and stirred overnight. The reaction was concentrated under reduced pressure in 10 mL. The residue was then diluted with ethyl acetate and washed with 5% citric acid (3×250 mL), saturated sodium bicarbonate (3×250 mL), and saturated sodium chloride (1×250 mL), dried over magnesium sulfate, filtered, and concentrated under reduced pressure to yield a pale yellow powder. The powder was collected and washed with ether, followed by drying under reduced pressure to yield (871 mg, 83%). $^1$H NMR (400 Hz, DMSO): δ 9.97 (s, 1H), 8.78 (t, 1H), 7.75 (m, 3H), 7.58 (d, 2H), 7.38 (d, 1H), 7.05 (d, 1H), 6.78 (d, 2H), 4.35 (d, 2H), 3.88 (d, 2H), 1.61–1.77 (m, 6H), 1.15–1.05 (m, 5H); Mass Spectrum (Chemical Ionization, 1% $NH_3$ in $CH_4$) m/z 383 (M+H).

Step 6: Phosphoric acid mono-[4- (3-carbamoyl-4-cyclohexylmethoxy-benzylcarbamoyl)-phenyl] ester The title compound was synthesized in a manner similar to that described for Example 1. The product was obtained as a colorless powder (50 mg). HPLC 92%, rt=17.2 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 461.5 (M–H).

EXAMPLE 45

[4-(3-Carbamoyl-4-cyclohexylmethoxy-benzylcarbamoyl)-phenyl]-difluoro-methyl-phosphonic acid

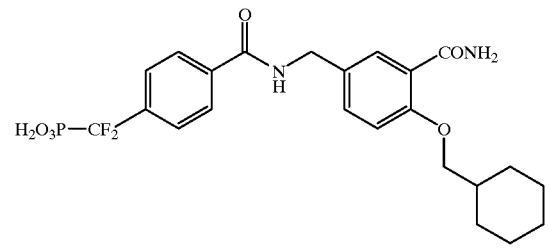

Step 1: [Difluoro-(4-iodo-phenyl)--methyl]-phosphonic acid diethyl ester

[Difluoro-(4-iodo-phenyl)-methyl]-phosphonic acid diethyl ester can be prepared in accordance with methods well known to those skilled in the art. (See, for example, Burke, et al., *J. Org. Chem.*, 1993;58: 1336–1340.)

Step 2: [Difluoro-(4-formyl-phenyl)-methyl]-phosphonic acid diethyl ester

To a solution of [Difluoro-(4-iodo-phenyl)-methyl]-phosphonic acid diethyl ester (1.6 g, 4.1 mmol) in anhydrous ether (40 mL) at –78° C. was added dropwise n-butyl lithium (2.5 M in hexanes, 2.5 mL, 6.1 mmol). The brown solution was stirred at –78° C. for 2 minutes. Ethyl formate (0.66 mL, 8.2 mmol) was then added, and the reaction was stirred for 10 minutes at –78° C. The mixture was then quenched with saturated ammonium chloride (10 mL) and warmed to room temperature. The reaction was then diluted with ether. The organic layers were washed with saturated sodium chloride (20 mL), dried over magnesium sulfate, filtered, and concentrated under reduced pressure to yield a yellow oil. Chromatography of the residue [3:7, ethyl acetate:hexanes] gradient to (1:1)] afforded the aldehyde (268 mg, 22%) as a clear oil. $^1$H NMR (400 MHz, DMSO): δ 10.28 (s, 1H), 8.25 (d, 2H), 7.97 (d, 2H), 4.42 (m, 4H), 1.40 (t, 6H).

Step 3: 4-[(Diethoxy-phosphoryl)-difluoro-methyl]-benzoic acid

To a solution of [Difluoro-(4-formyl-phenyl)-methyl]-phosphonic acid diethyl ester (260 mg, 0.9 mmol) in acetone (25 mL) at room temperature was added Jones reagent (5 mL). The reaction was quenched by addition of ethanol (5 mL). The reaction was then concentrated under reduced pressure to 5 mL. The residue was diluted with ethyl acetate and washed with water (2×20 mL), saturated sodium chloride (20 mL), dried over magnesium sulfate, filtered, and concentrated under reduced pressure to yield a white crystalline solid (268 mg, 98%). $^1$H NMR (400 MHz, DMSO): δ 8.09 (d, 2H), 7.70 (d, 2H), 4.15 (m, 4H), 1.22 (t, 6H); Mass Spectrum (Chemical Ionization, 1% NH in $CH_4$) m/z 309 (M+H).

Step 4: [4-(3-Carbamoyl-4-cyclohexylmethoxy-benzylcarbamoyl)-phenyl]-difluoro-methyl-phosphonic acid The title compound was synthesized in a manner similar to that described for Example 44. The product was obtained as a colorless powder (39 mg). HPLC 100%, rt=17.4 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 495.4 (M–H).

EXAMPLE 46

Phosphoric acid mono-[4-(3-carbamoyl-4-cyclohexylmethoxy-benzylcarbamoyl)-2,6-dimethyl-phenyl] ester

47

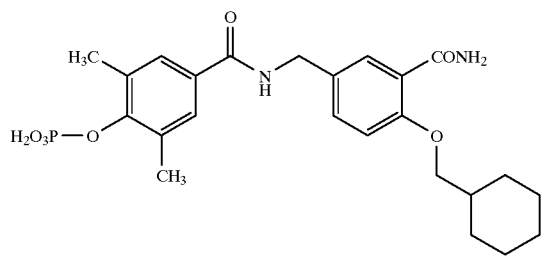

The title compound was synthesized in a manner similar to that described for Example 44. The product was obtained as a colorless powder (79 mg). HPLC 100%, rt=18.3 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 489.4 (M−H).

EXAMPLE 47

Phosphoric acid mono-[4-(3-carbamoyl-4-cyclohexyl-methoxy-benzylcarbamoyl)-2-chloro-phenyl] ester

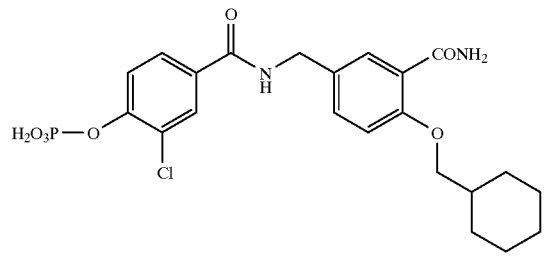

The title compound was synthesized in a manner similar to that described for Example 44. The product was obtained as a colorless powder (119 mg). HPLC 100%, rt=17.7 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 495.3 (M−H).

EXAMPLE 48

Phosphoric acid mono-[4-(4-cyclohexylmethoxy-3-methylcarbamoyl-benzylcarbamoyl)-phenyl] ester

48

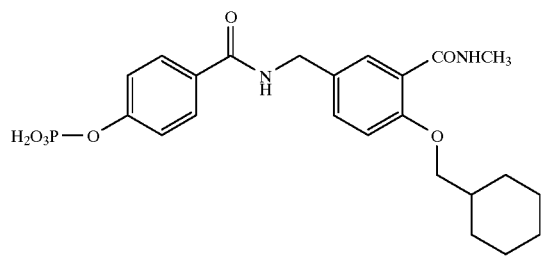

The title compound was synthesized in a manner similar to that described for Example 44. The product was obtained as a colorless powder (79 mg). HPLC 100%, rt=18.3 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 475.5 (M−H).

EXAMPLE 49

(S)-Phosphoric acid mono-{4-[2-acetylamino-2-(3-carbamoyl-4-cyclohexylmethoxy-benzylcarbamoyl)-ethyl]-phenyl} ester

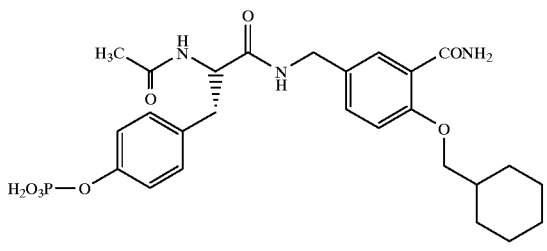

The title compound was synthesized in a manner similar to that described for Example 44. The product was obtained as a colorless powder (60 mg). HPLC 99%, rt=16.9 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 546.4 (M−H).

EXAMPLE 50

(S)-Phosphoric acid mono-(4-{2-acetylamino-2-[3-carbamoyl-4-(3,5-dimethyl-benzyloxy)-benzylcarbamoyl]-ethyl}-phenyl) ester

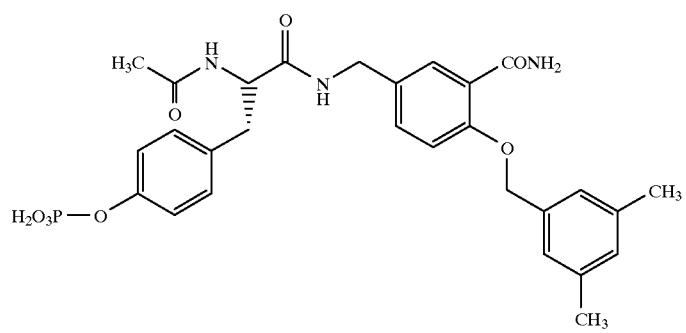

The title compound was synthesized in a manner similar to that described for Example 44. The product was obtained as a colorless powder (59 mg). HPLC 98%, rt=17.0 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 568.4 (M−H).

EXAMPLE 51
Phosphoric acid mono-(4-{(S)-2-acetylamino-2-[(RS)-1-(3-carbamoyl-4-cyclohexylmethoxy-phenyl)-ethylcarbamoyl]-ethyl}-phenyl) ester

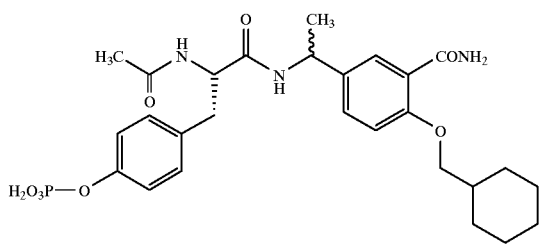

The title compound was synthesized in a manner similar to that described for Example 44. The product was obtained as a-colorless powder (61 mg). HPLC 99%, rt=19.7 and 20.10 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 560.4 (M−H).

Alternatively, the title compound can be synthesized as follows:

Step 1: 5-Acetyl-2-hydroxy-benzamide

The title compound was synthesized in a manner similar to that described for Example 44, Step 3. The product was obtained as a solid. $^1$H NMR (400 MHz, DMSO): δ 13.84 (s, 1H), 8.73 (bs, 1H), 8.53 (s, 1H), 8.12 (bs, 1H), 8.00 (d, 1H), 6.99 (d, 1H), 2.59 (s, 3H). Mass Spectrum (Chemical Ionization, 1% NH$_3$ in CH$_4$) m/z 179 (M+H).

Step 2: 5-Acetyl-2-cyclohexylmethoxy-benzamide

The title compound was synthesized in a manner similar to that described for Example 44, Step 4. The product was obtained as a solid. $^1$H NMR (400 MHz, DMSO): δ 8.31 (s, 1H), 8.05 (d, 1H), 7.22 (d, 1H), 4.04 (d, 2H), 2.53 (s, 3H), 1.83 (m, 6H), 1.14 (m, 5H).Mass Spectrum (Chemical Ionization, 1% NH$_3$ in CH$_4$) m/z 275 (M+H).

Step 3: (E/Z)-2-Cyclohexylmethoxy-5-(1-hydroxyimino-ethyl)-benzamide

To a solution of 5-acetyl-2-cyclohexylmethoxy-benzamide (1.0 g, 3.63 mmol) in pyridine (25 mL) at room temperature was added hydroxylamine hydrochloride (0.38 g, 5.45 mmol). The reaction was stirred 48 hours. The reaction was then concentrated under reduced pressure, diluted with ethyl acetate and washed with 5% citric acid (3×100 mL), saturated sodium chloride (1×100 mL), dried over magnesium sulfate, filtered, and concentrated under reduced pressure to yield a foam. $^1$H NMR (400 MHz, DMSO): δ 11.07 (s, 1H), 8.08 (d, 1H), 7.72 (d, 1H), 7.61 (bs, 1H), 7.53 (bs, 1H), 7.14 (d, 1H), 4.03 (d, 2H), 2.13 (s, 3H), 1.74 (m, 6H), 1.11 (m, 5H). Mass Spectrum (Chemical Ionization, 1% NH$_3$ in CH$_4$) m/z 291 (M+H).

Step 4: (+/−)-5-(1-Amino-ethyl)-2-cyclohexylmethoxy-benzamide

To a solution of (E/Z)-2-Cyclohexylmethoxy-5-(1-hydroxyimino-ethyl)-benzamide (0.50 g, 1.72 mmol) in methanol (20 mL) and triethylamine (5 mL) was added wet Raney Nickel (0.30 g) under hydrogen at 45 psi for 16.5 hours. The reaction was then concentrated under reduced pressure to yield a white solid. $^1$H NMR (400 MHz, DMSO): δ 7.86 (s, 1H), 7.59 (d, 2H), 7.47 (d, 1H), 7.10 (d, 1H), 4.03 (q, 1H), 3.97 (d, 2H), 1.83 (m, 6H), 1.23 (m, 8H). Mass Spectrum (Chemical Ionization, 1% NH$_3$ in CH$_4$) m/z 277 (M+H).

Phosphoric acid mono-(4-{(S)-2-acetylamino-2-[(RS)-1-(3-carbamoyl-4-cyclohexylmethoxy-phenyl)-ethylcarbamoyl]-ethyl}-phenyl) ester The title compound was synthesized in a manner similar to that described for Example 44. The product was obtained as a colorless powder (61 mg). HPLC 99%, rt=19.7 and 20.1 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 560.4 (M−H).

EXAMPLE 52
(S)-Phosphoric acid mono-{4-[2-acetylureido-2-(3-carbamoyl-4-cyclohexylmethoxy-benzylcarbamoyl)-ethyl]-phenyl} ester

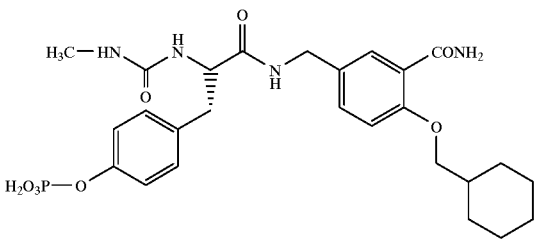

Step 1: (S)-3-(4-Benzyloxy-phenyl)-2-(3-methyl-ureido)-propionic acid benzyl ester This compound was synthesized in a manner similar to that described in Example 7 (Step 1).

Step 2: (S)-3-(4-Hydroxy-phenyl)-2-(3-methyl-ureido)-propionic acid

This compound was synthesized in a manner similar to that described in Example 7 (Step 2).

Step 3: (S)-2-Cyclohexylmethoxy-5-{[3-(4-hydroxy-phenyl)-2-(3-methyl-ureido)-propionylaminol-methyl}-benzamide This compound was synthesized in a manner similar to that described in Example 44 (Step 2).

Step 4: (S)-Phosphoric acid mono-{4-[2-acetylureido-2-(3-carbamoyl-4-cyclohexylmethoxybenzylcarbamoyl)-ethyl]-phenyl} ester The title compound was synthesized in a manner similar to that described for Example 1. Product was obtained as a white solid (100 mg). HPLC 98%, rt=17.4 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 561.4 (M−H).

EXAMPLE 53

(S)-{4-[2-Acetylamino-2-(3-carbamoyl-4-cyclohexyl-methoxy-benzylcarbamoyl)-ethyl]-phenyl}-difluoro-methyl-phosphonic acid

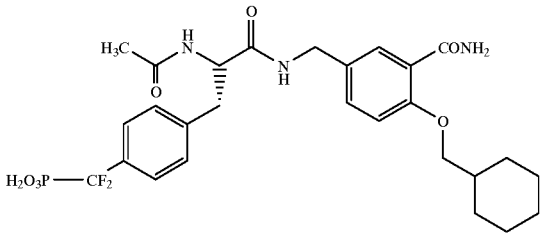

The title compound was synthesized in a manner similar to that described for Example 49 and cleaved according to Example 5 (Step 2). The product was obtained as a colorless powder (3.8 mg). HPLC 97%, rt=17.6 minutes, C18, column eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 580.5 (M−H).

EXAMPLE 54

[S-(R*,R*)]4-[2-Acetylamino-3-(4-phosphono-phenyl)-propionylamino]-4-[(3-cyclohexyl-propyl)-methyl-carbamoyl]-butyric acid or Ac-(4-phosphonyl)-L-Phe-L-Glu-N(methyl)(3-cyclohexylpropyl)

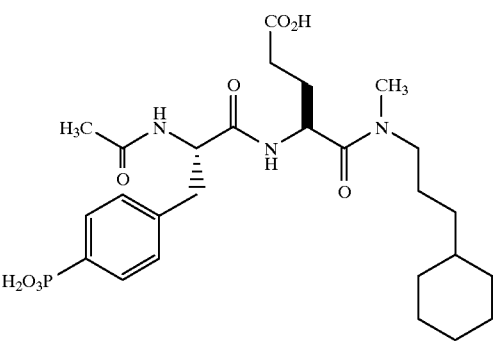

The title compound was synthesized in a manner similar to that described for Example 34. The product was obtained as a colorless powder (125 mg). HPLC 100%, rt=12.4 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 552 (M−H).

EXAMPLE 55

[S-(R*,R*)]-2,2-Dimethyl-propionic acid {[4-(2-acetylamino-2-{1-[(3-cyclohexyl-propyl)-methyl-carbamoyl]-propylcarbamoyl}-ethyl)-phenyl]-difluoro-methyl}-hydroxy-phosphinoyloxymethyl ester

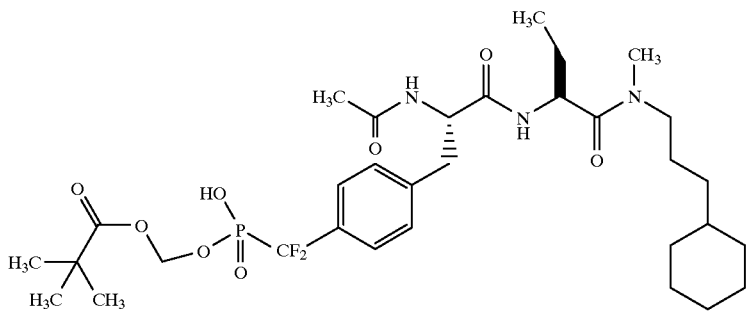

Ac-(4-(difluorophosphonomethyl))-L-Phe-L-Abu-N(methyl) (3-cyclohexylpropyl) (from Example 10) (0.15 mmol, 84 mg) was dissolved in 2 mL dimethylformamide and treated with diisopropylethylamine (0.5 mmol, 81 μL) and chloromethyl pivaloate (1.5 mmol, 214 μL). The reaction mixture was stirred at 70° C. for 24 hours. The reaction mixture was diluted with 3 mL of dimethylformamide and purified by preparative HPLC, as previously described, to provide the product as a colorless solid after lyophilization (58 mg). HPLC 100%, rt=14.8 minutes, C18, column eluting with a gradient of 0% to 100% acetonitrile containing 0.1% TFA and water containing 0.1% TFA over 20 minutes. Electrospray Mass Spectrum (50/50 acetonitrile/water+ 0.1% ammonium hydroxide) m/z 672 (M–H).

EXAMPLE 56

[S-(R*,R*)]-4-[2-Acetylamino-3-(4-phosphonooxy-phenyl)-propionylamino]-4-(2-adamantan-1-yl-ethylcarbamoyl)-butyric acid

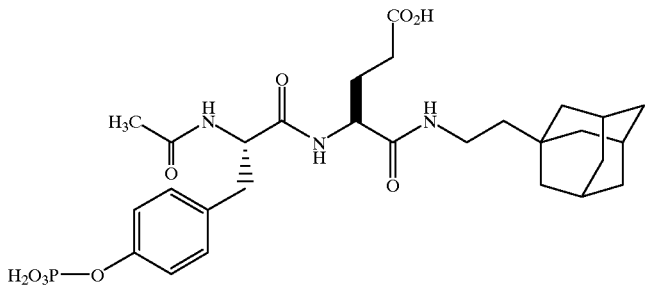

The title compound was synthesized in a manner similar to that described for Example 1. The product was obtained as a white solid (50 mg). HPLC 100%, rt=18.0 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 593 (M–H).

EXAMPLE 57

(S)-Phosphoric acid mono-(4-{2-acetylamino-2-[1-ethyl-1-(3-phenyl-propylcarbamoyl)-propylcarbamoyl]-ethyl}-phenyl) ester

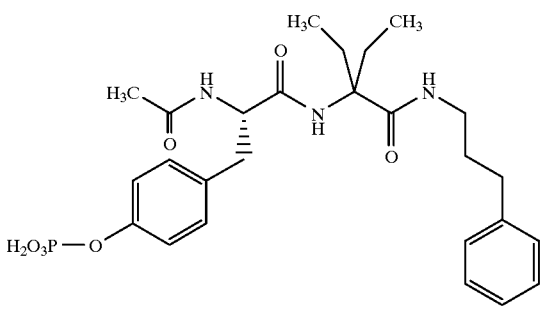

The title compound was synthesized in a manner similar to that described for Example 1. The product was obtained as a white solid (150 mg). HPLC 100%, rt=18.0 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 532 (M–H).

EXAMPLE 58

[S-(R*,R*)]-Phosphoric acid mono-(4-{2-acetylamino-2-[2-hydroxy-1-(3-phenyl-propylcarbamoyl)-propylcarbamoyl]-ethyl}-phenyl) ester

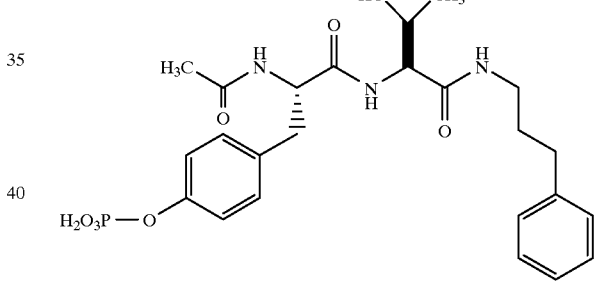

The title compound was synthesized in a manner similar to that described for Example 1. The product was obtained as a white solid (46 mg). HPLC 100%, rt=13.8 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 520 (M–H).

EXAMPLE 59

[S-(R*,R*)]-4-[(3-Cyclohexyl-propyl)-methyl-carbamoyl]-4-[2-(3,3-dimethyl-ureido)-3-(4-phosphonooxy-phenyl)-propionylaminol-butyric acid or N-[(Dimethylamino)carbonyl]-(O-phosphono)-L-Tyr-L-Glu-N(methyl)(3-cyclohexylpropyl)

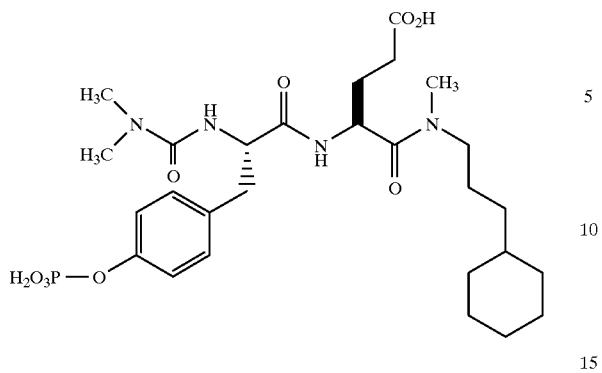

The title compound was synthesized in a manner similar to that described for Example 7. The product was obtained as a colorless solid (110 mg). HPLC 100%, rt=17.9 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 597 (M–H).

EXAMPLE 60

5-[(3-cyclohexylpropyl)methylamino]-4-[[2-[[(dimethylamino)-sulfonyl]amino]-1-oxo-3-[4-(phosphonooxy)phenyl]propyl]amino]-5-oxo-pentanoic acid

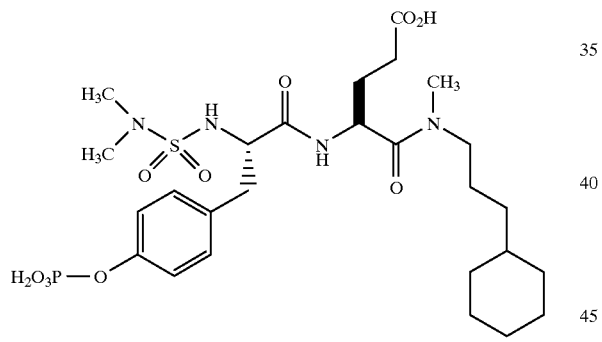

The title compound was synthesized in a manner similar to that described for Example 33. The product was obtained as a white solid (115 mg). HPLC 100%, rt=20.7 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 633 (M–H).

EXAMPLE 61

(S)-4-[(3-Cyclohexyl-propyl)--methyl-carbamoyl]-4- [3-(4-phosphonooxy-benzyl)-ureido]-butyric acid

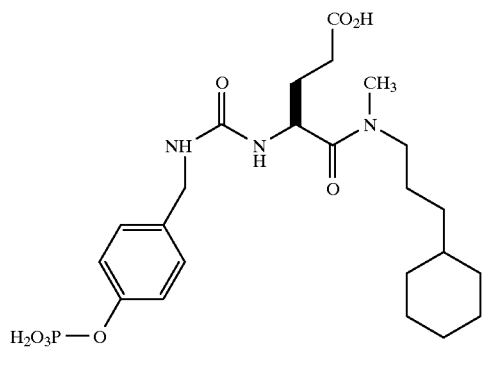

The title compound was synthesized in a manner similar to that described in Example 35. The product was obtained as a colorless solid (47 mg). HPLC 98%, rt=17.8 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 512 (M–H).

EXAMPLE 62

(S)-4-[(3-Cyclohexyl-propyl)-methyl-carbamoyl]-4-(4-phosphonooxy-benzoylamino)-butyric acid

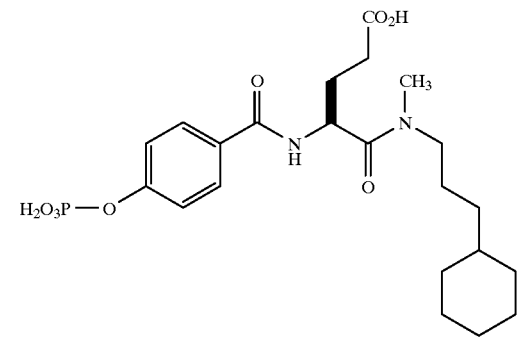

The title compound was synthesized in a manner similar to Example 1 and 39. The product was obtained as a colorless solid (70 mg). HPLC 95%, rt=17.6 minutes, C18, eluting with a gradient of 0% to 66% acetonitrile containing 0.1% TFA and water containing 0.1% TFA over 22 minutes. Electrospray Mass Spectrum (50/50 acetonitrile/water+ 0.1% ammonium hydroxide) m/z 483 (M–H).

EXAMPLE 63a

[S-(R*,R*)]- or [S-(R*,S*)]-[(4-{2-Acetylamino-2-[1-(3-carbamoyl-4-cyclohexylmethoxy-phenyl)-ethylcarbamoyl]-ethyl]-phenyl)-difluoro-methyl]-phosphonic acid

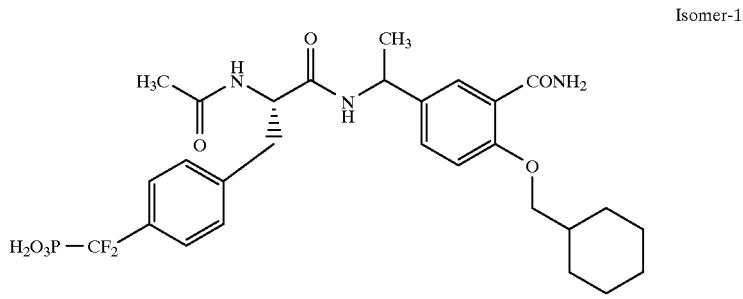

Isomer-1

The title compound was synthesized in a manner similar to that described for Example 51 and 53, except in this case the mixture of diastereomers was separated by preparative HPLC as previously described. The product was obtained as a colorless powder (31 mg). HPLC 100%, rt=12.6 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 594 (M−H).

EXAMPLE 63b

[S-(R*,R*)]- or [S-(R*,S*)]-[(4-{2-Acetylamino-2-[1-(3-carbamoyl-4-cyclohexylmethoxy-phenyl)-ethylcarbamoyl]-ethyl}-phenyl)-difluoro-methyl]-phosphonic acid

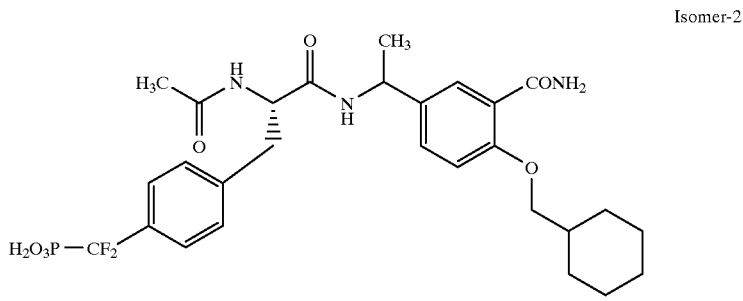

Isomer-2

The title compound is the second isomer separated in Example 51 and 53. The product was obtained as a colorless powder (34 mg). HPLC>95%, rt=12.8 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 594 (M−H).

EXAMPLE 64a

Phosphoric acid mono-[4-(2-acetylamino-2-{1-[3-carbamoyl-4-(2-cyclohexyl-1-methyl-ethoxy)-phenyl]-ethylcarbamoyl}-ethyl)-phenyl] ester

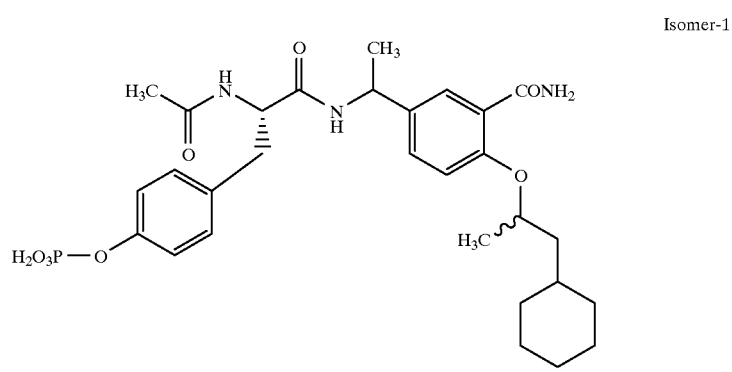

Isomer-1

The title compound was synthesized in a manner similar to that described for Example 51, except in this case the mixture of diastereomers was separated by preparative HPLC as previously described. The product was obtained as a colorless powder (5 mg). HPLC 100%, rt=13.1 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 588 (M−H).

EXAMPLE 64b

Phosphoric acid mono-[4-(2-acetylamino-2-{1-[3-carbamoyl-4-(2-cyclohexyl-1-methyl-ethoxy)-phenyl]-ethylcarbamoyl}-ethyl)-phenyl] ester Isomer-2

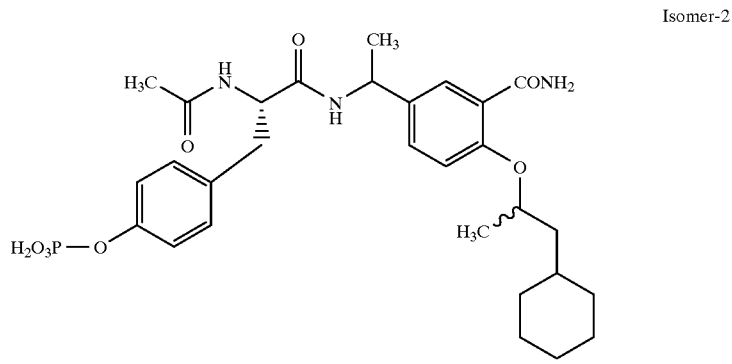

The title compound was synthesized in a manner similar to that described for Example 51, except in this case the mixture of diastereomers was separated by preparative HPLC as previously described. The product was obtained as a colorless powder (4 mg). HPLC 100%, rt=13.3 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 588 (M−H).

EXAMPLE 65

(S)-Phosphoric acid mono-(4-{2-acetylamino-2-[(RS)-1-(3-carbamoylmethyl-4-cyclohexylmethoxy-phenyl)-ethylcarbamoyl]-ethyl}-phenyl) ester

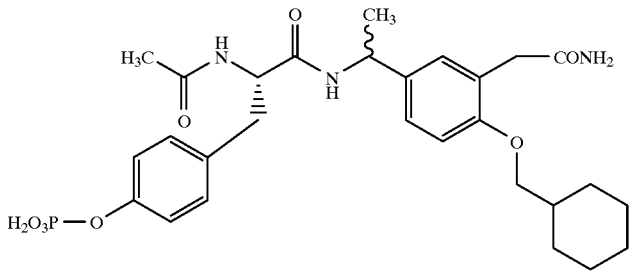

Step 1: (2-hydroxy-phenyl)-acetic acid methyl ester

To a solution of 2-hydroxyphenylacetic acid (20.0 g, 129.7 mmol) in 250 mL of methanol was bubbled at room temperature anhydrous hydrochloric acid for 5 minutes. The reaction was capped and stirred overnight. The reaction was then concentrated under reduced pressure to yield a pale oil (20.5 g, 95%). $^1$H NMR (300 MHz, DMSO): δ 9.45 (s, 1H), 7.15 (m, 2H), 6.75 (m, 2H), 3.57 (d, 2H), 3.35 (s, 3H).

Step 2: (2-methoxy-phenyl)-acetic acid methyl ester

To a solution of (2-hydroxy-phenyl)-acetic acid methyl ester (20.0 g, 120.5 mmol) in 200 mL N,N-dimethylformamide was added freshly ground potassium carbonate (24.9 g, 180.7 mmol) followed by iodomethane (8.25 mL, 132.5 mmol). The reaction mixture was heated to 50° C. overnight. The reaction was then concentrated under reduced pressure. The residue was diluted with ethyl acetate and water. The organic layer was washed with 1N hydrochloric acid (2×100 mL) and saturated sodium chloride (1×100 mL), dried over magnesium sulfate, filtered, and concentrated under reduced pressure. Chromatography of the residue (1:4, ethyl acetate/hexanes) gave the product as a clear oil. $^1$H NMR (400 MHz, DMSO): δ 7.25 (t, 1H), 7.17 (d, 1H), 6.97 (d, 1H), 6.89 (t, 1H), 3.74 (s, 3H), 3.58 (s, 5H). Mass Spectrum (Chemical Ionization, 1% NH$_3$ in CH$_4$) m/z 180 (M+H).

Step 3: (5-acetyl-2-hydroxy-phenyl)-acetic acid methyl ester

To a solution of aluminum chloride (35.0 g, 262.5 mmol) in dichloromethane (75 mL) was added a solution of (2-Methoxy-phenyl)-acetic acid methyl ester (13.5 g, 75.0 mmol) and acetyl chloride (5.86 mL, 82.5 mmol)in dichloromethane (75 mL) dropwise. After the addition was complete the reaction was heated to reflux for 5 hours. The reaction mixture was then cooled and carefully poured onto a mixture of ice and water. The aqueous layer was then extracted with ethyl acetate (2×400 mL). The combined extracts were then washed with saturated sodium chloride (1×100 mL), dried over magnesium sulfate, filtered, and concentrated under reduced pressure to yield a solid. $^1$H NMR (400 MHz, DMSO): δ 10.51 (s, 1H), 7.79 (m, 2H), 6.88 (d, 1H), 3.63 (s, 2H), 3.59 (s, 3H), 2.47 (s, 3H). Mass Spectrum (Chemical Ionization, 1% NH₃ in CH₄) m/z 209 (M+H).

Step 4: (5-acetyl-2-cyclohexylmethoxy-phenyl)-acetic acid methyl ester

This compound was synthesized in a manner similar to that described for Example 44, Step 4. The product was obtained as an oil (7.9 g). ¹H NMR (400 MHz, DMSO): δ 7.89 (d, 1H), 7.84 (S, 1H), 7.05 (d, 1H), 3.86 (d, 2H), 3.66 (s, 2H), 3.58 (s, 3H), 2.49 (s, 3H), 1.81 (m, 6H), 1.12 (m, 5H). Mass Spectrum (Chemical Ionization, 1% NH₃ in CH₄) m/z 305 (M+H).

Step 5: (5-Acetyl-2-cyclohexylmethoxy-phenyl)-acetic acid

To a solution of (5-Acetyl-2-cyclohexylmethoxy-phenyl)-acetic acid methyl (7.9 g, 25.9 mmol) in tetrahydrofuran (150 mL) and methanol (150 mL) was added a 1N solution of sodium hydroxide (52.0 mL, 52 mmol). The reaction was stirred at room temperature overnight. The reaction was then concentrated under reduced pressure, diluted with ethyl acetate and acidified to pH 2 with 1N hydrochloric acid. The aqueous layer was extracted with ethyl acetate (3×200 mL). The combined extracts where then washed with saturated sodium chloride (1×200 mL), dried over magnesium sulfate, filtered, and concentrated under reduced pressure. ¹H NMR (400 MHz, DMSO): δ 12.23 (S, 1H), 7.89 (d, 1H), 7.81 (s, 1H), 7.04 (d, 1H), 3.86 (d, 2H), 3.56 (s, 2H), 2.49 (s, 3H), 1.71 (m, 6H), 1.16 (m, 5H). Mass Spectrum (Chemical Ionization, 1% NH₃ in CH₄) m/z 290 (M+H).

Step 6: 2-(5-Acetyl-2-cyclohexylmethoxy-phenyl)-acetamide

This compound was synthesized in a manner similar to that described for Example 44, Step 3. The product was obtained as a solid. ¹H NMR (400 MHz, DMSO): δ 7.85 (d, 1H), 7.77 (s, 1H), 7.33 (bs, 1H), 7.01 (bs, 1H), 6.89 (s, 1H), 3.85 (d, 2H), 3.42 (s, 2H), 2.50 (s, 3H), 1.72 (m, 6H), 1.16 (m, 5H). Mass Spectrum (Chemical Ionization, 1% NH₃ in CH₄) m/z 289 (M+H).

Step 7: (E/Z)-2-(2-cyclohexylmethoxy-5-(1-hydroxyimino-ethyl)-phenyl)-acetamide

This compound was synthesized in a manner similar to that described for Example 51, Step 3. The product was obtained as a solid. ¹H NMR (400 MHz, DMSO): δ 10.92 (s, 1H), 7.45 (m, 2H), 7.26 (bs, 1H), 6.90 (d, 1H), 6.85 (bs, 1H), 3.75 (d, 2H), 3.37 (s, 2H), 3.33 (s, 3H), 1.72 (m, 6H), 1.16 (m, 5H). Mass Spectrum (Chemical Ionization, 1% NH₃ in CH₄) m/z 304 (M+H).

Step 8: (+/-)-2-(5-(1-Amino-ethyl)-2-cyclohexylmethoxy-phenyl)-acetamide

This compound was synthesized in a manner similar to that described for Example 51, Step 4. The product was obtained as a solid. ¹H NMR (400 MHz, DMSO): δ 7.11 (m,2H), 6.88 (m, 1H), 3.90 (q, 1H), 3.71 (d, 2H), 3.37 (s, 2H), 1.72 (m, 6H), 1.20 (m, 8H). Mass Spectrum (Chemical Ionization, 1% NH₃ in CH₄) m/z 290 (M+H).

Step 9:(S)-Phosphoric acid mono-(4-{2-acetylamino-2-[(RS)-1-(3-carbamoylmethyl-4-cyclohexylmethoxy-phenyl)-ethylcarbamoyl]-ethyl}-phenyl) ester The title compound was synthesized in a manner similar to that described for Example 44. The product was obtained as a colorless powder (93 mg). HPLC 100%, rt=17.8 and 18.0 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 574 (M–H).

EXAMPLE 66

Phosphoric acid mono-(4-{(S)-2-acetylamino-2-[3-carbamoyl-4-(2-cyclohexyl-(RS)-1-methyl-ethoxy)-benzylcarbamoyl]-ethyl}-phenyl) ester

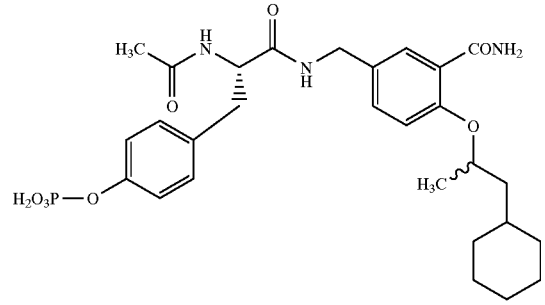

The title compound was synthesized in a manner similar to that described in Example 44. The product was obtained as a colorless solid (101 mg). HPLC 98%, rt=18.9 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 574 (M–H).

EXAMPLE 67

Phosphoric acid mono-(4{(S)-2-acetylamino-2-[(RS)-1-(3-carbamoyl-4-cyclohexylmethoxy-phenyl)-2-phenyl-ethylcarbamoyl]-ethyl}-phenyl) ester

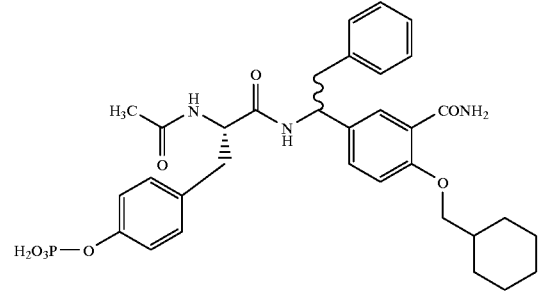

The title compound was synthesized in a manner similar to that described for Example 65 starting at step 3. The product was obtained as a colorless powder (26 mg). HPLC 100%, rt=20.2 and 20.5 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 636 (M–H).

EXAMPLE 68

Phosphoric acid mono-[4-((S)-2-acetylamino-2-{(RS)-1-[3-carbamoyl-4-(3,5-dimethyl-benzyloxy)-phenyl]-ethylcarbamoyl}-ethyl)-phenyl] ester

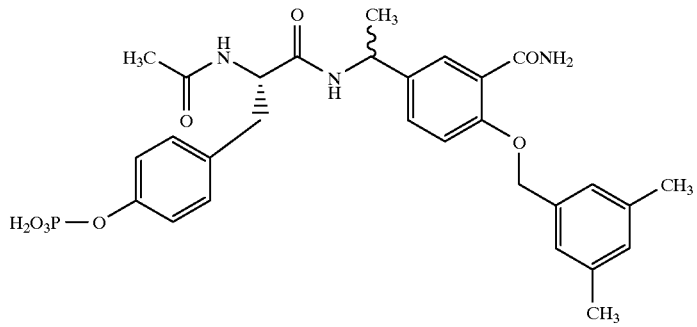

The title compound was synthesized in a manner similar to that described for Example 51. The product was obtained as a colorless powder (16 mg). HPLC 90%, rt=16.9 and 17.3 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 582 (M–H).

EXAMPLE 69

Phosphoric acid mono-(4-{(S)-2-acetylamino-2-[(RS)-1-(3-carbamoyl-4-cyclohexylmethoxy-phenyl)-butylcarbamoyl]-ethyl}-phenyl) ester

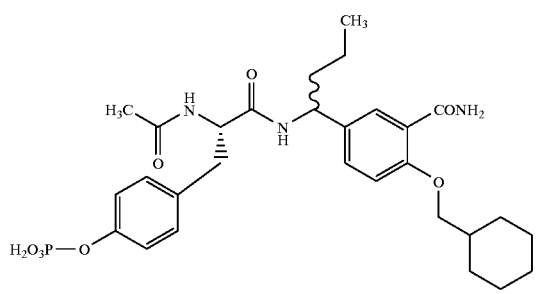

The title compound was synthesized in a manner similar to that described for Example 65 starting at step 3. The product was obtained as a colorless powder (32 mg). HPLC 100%, rt=19.2 and 19.5 minutes, C18, column eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 588 (M–H).

EXAMPLE 70

(S)-Phosphoric acid mono-{4-[2-acetylamino-2-(4-cyclohexylmethoxy-3-hydroxycarbamoyl-benzylcarbamoyl)-ethyl]-phenyl} ester

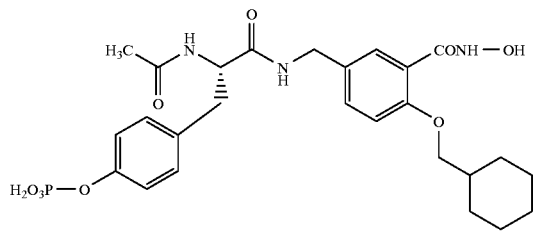

The title compound was synthesized in a manner similar to that described in Example 44, except that t-butyl-hydroxylamine was used instead of ammonia. This protecting group was not removed until the final deprotection step to give the product as a colorless solid (11 mg). HPLC 92%, rt=19.6 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 562 (M–H).

EXAMPLE 71

(S)-Phosphoric acid mono-{4-[2-acetylamino-2-(4-cyclohexylmethoxy-3-hydrazinocarbonyl-benzylcarbamoyl)-ethyl]-phenyl} ester

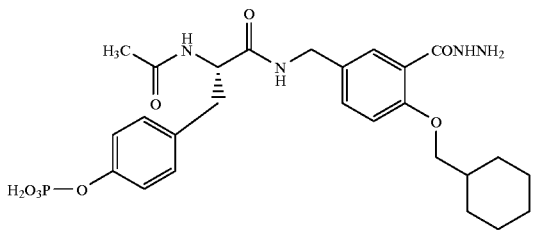

The title compound was synthesized in a manner similar to that described in Example 44, except that Boc-hydrazine was used instead of ammonia. This protecting group was not removed until the final deprotection step to give the product as a colorless solid (263 mg). HPLC 96%, rt=14.4 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 561 (M–H).

EXAMPLE 72

(S)-Phosphoric acid mono-(4-{2-acetylamino-2-[3-carbamoyl-4-(2-ethyl-benzyloxy)-benzylcarbamoyl]-ethyl}-phenyl) ester

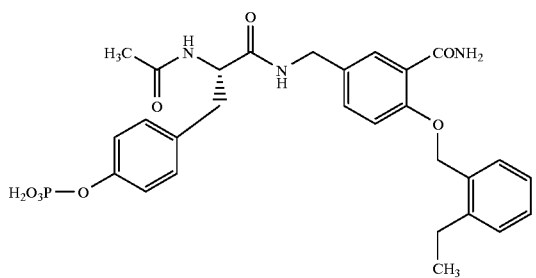

The title compound was synthesized in a manner similar to that described in Example 44. The product was obtained as a colorless solid (58 mg). HPLC 100%, rt=16.8 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 568 (M−H).

EXAMPLE 73
(4-{(S)-2-Acetylamino-2-[(RS)-1-(3-carbamoyl-4-cyclohexylmethoxy-phenyl)-ethylcarbamoyl]-ethyl}-phenyl)-phosphonic acid

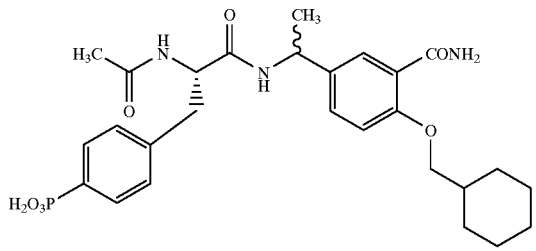

The title compound was synthesized in a manner similar to that described for Example 51 and 53. The product was obtained as a colorless powder (5 mg). HPLC rt=12.3 and 12.5 minutes, C18, column eluting with a gradient of 0% to 100% acetonitrile containing 0.1% TFA and water containing 0.1% TFA over 20 minutes. Electrospray Mass Spectrum (50/50 acetonitrile/water+0.1% ammonium hydroxide) m/z 544 (M−H).

EXAMPLE 74
Phosphoric acid mono-{4-[3-(3-carbamoyl-4-cyclohexylmethoxy-benzyl)-ureido]-phenyl} ester

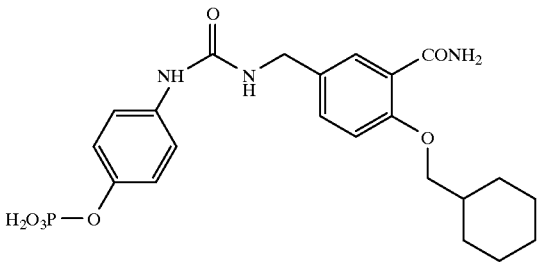

Step 1: 1-isocyanato-4(phenylmethoxy)benzene
To amine (21.20 mmol, 5.0 g) in toluene (10 ml) at room temperature was added phosgene in toluene (1.93 M, 106 mmol, 54 mL). After refluxing 12 hours, the mixture was evaporated to dryness under reduced pressure. The crude product was used directly in the next step without further purification or characterization.

Step 2: 5-[3-(4-Benzyloxy-phenyl)-ureidomethyl]-2-cyclohexylmethoxy-benzamide
This compound was synthesized in a manner similar to that described in Example 7 (step 1).
Step 3: 2-Cyclohexylmethoxy-5-[3-(4-hydroxy-phenyl)-ureidomethyl]-benzamide
This compound was synthesized in a manner similar to that described in Example 6 (step 2).
Step 4: Phosphoric acid mono-{4-[3-(3-carbamoyl-4-cyclohexylmethoxy-benzyl)-ureido]-phenyl} ester
The title compound was synthesized in a manner similar to that described for Example 1. The product was obtained as a white solid (49 mg). HPLC 100%, rt=17.6 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 476 (M−H).

EXAMPLE 75
(+/−)-Phosphoric acid mono-(5-{3-[1-(3-carbamoyl-4-cyclohexylmethoxy-phenyl)-ethyl]-ureido}-naphthalen-2-yl) ester

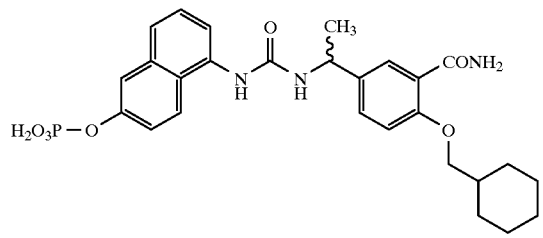

The title compound was synthesized in a manner similar to that described for Example 74. The product was obtained as a white solid (38 mg). HPLC 100%, rt=19.2 minutes, C18, eluting with a gradient of 0% to 66% acetonitrile containing 0.1% TFA and water containing 0.1% TFA over 22 minutes. Electrospray Mass Spectrum (50/50 acetonitrile/water+0.1% ammonium hydroxide) m/z 540 (M−H).

EXAMPLE 76
Phosphoric acid mono-{4-[3-(3-carbamoyl-4-cyclohexylmethoxy-benzyl)-ureidomethyl]-phenyl} ester

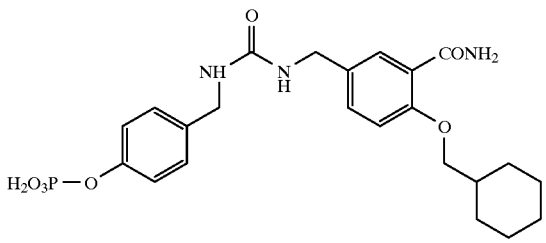

The title compound was synthesized in a manner similar to that described in Example 35 only the amine hydrochloride produced in Example 44 step 5 was employed as a partner in the urea forming reaction. The product was obtained as a colorless solid (78 mg). HPLC 98%, rt=17.5 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 490 (M−H).

EXAMPLE 77
[S-(R*,R*)]- or [S-(R*,S*)]-2,2-Dimethyl-propionic acid {[(4-{2-Acetylamino-2-[1-(3-carbamoyl-4- cyclohexylmethoxy-phenyl)-ethylcarbamoyl]-ethyl}-phenyl)-difluoro-methyl} hydroxy-phosphinoyloxymethyl ester binding of $^{125}$I-labeled Glu-Pro-Gln-(4-(difluorophosphonomethyl))-Phe-Glu-Glu-Ile-Pro-Ile-Tyr-Leu to a glutathione-S-transferase(GST)-Abl SH2 fusion Isomer-1

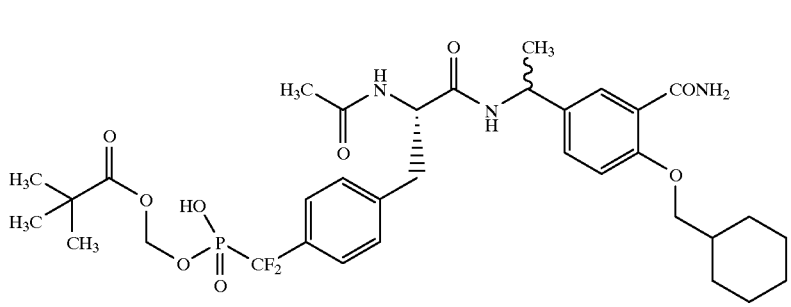

The title compound was synthesized in a manner similar to that described in Example 55. The product was obtained as a colorless solid (6 mg). HPLC 100%, rt=18.8 minutes, C18, eluting with a gradient of 0% to 66% acetonitrile containing 0.1% TFA, and water containing 0.1% TFA over 22 minutes. Electrospray Mass Spectrum (50/50 acetonitrile/water+0.1% ammonium hydroxide) m/z 708 (M–H).

Inhibition of $^{125}$I-Phosphopeptide Binding to Immobilized Src SH2

The binding affinities of compounds of the present invention to Src SH2 was determined using a competitive radiolabeled phosphopeptide displacement assay. Specifically, binding of $^{125}$I-labeled Glu-Pro-Gln-pTyr-Glu-Glu-Ile-Pro-Ile-Tyr-Leu or $^{125}$I-labeled Glu-Pro-Gln-(4-(difluorophosphonomethyl))-Phe-Glu-Glu-Ile-Pro-Ile-Tyr-Leu to a glutathione-S-transferase(GST)-Src SH2 fusion protein was performed in 20 mM Tris (pH 7.5), 150 mM NaCl, 5 mM EDTA, and 0.1% NP-40. Assay additions to a Millipore filter plate (0.45 mM PVDF) resulted in Src SH2 fusion protein-glutathione sepharose bead complex, 2.8 nM $^{125}$I-phosphopeptide and 2% DMSO+test compound at different concentrations. Binding was performed at room temperature for 20 minutes while continuously inverting the plate. Unbound $^{125}$I-phosphopeptide was separated from SH2-bound radiolabeled peptide by vacuum filtration and washing two times with 100 μL per well of assay buffer. Results are expressed as $IC_{50}$ values in Table 1 below.

Inhibition of Activated PDGF Receptor Binding to $^{35}$S-SH2 Domains

The binding of compounds of the present invention have been determined using $^{35}$S-labeled GST SH2 protein constructs and their binding to an immobilized PDGF receptor kinase domain. Binding of $^{35}$S-X-SH2-GST (X=Src, Abl, Grb2, p85-N, p85-C, Syp-N, and PLCγ-C domains) to immobilized PDGF receptor kinase domain was performed in a Millipore filter plate (0.45 mM PDVF) in 20 mM Tris buffer (pH 7.5), 150 mM NaCl, 10 mM mgCl$_2$, and 0.1% triton. The assay was conducted at room temperature for 30 minutes while continuously inverting the plate. The resultant SH2-GST-PDGF receptor kinase complex was separated from excess $^{35}$S-SH2-GST protein by vacuum filtration and the amount of bound SH2-GST was determined by scintillation counting. Results are expressed as $IC_{50}$ values and/or % inhibition at specified concentrations in Table 2 below.

Inhibition of $^{125}$I-Phosphopeptide Binding to Immobilized Abl SH2

The binding affinities of compounds of the present invention to Abl SH2 was determined using a competitive radiolabeled phosphopeptide displacement assay. Specifically, protein was performed in 20 mM Tris (pH 7.5), 150 mM NaCl, 5 mM EDTA, and 0.1% NP-40. Assay additions to a Millipore filter plate (0.45 mM PVDF) resulted in Abl SH2 fusion protein-glutathione sepharose bead complex, 2.8 nM $^{125}$I-phosphopeptide and 2% DMSO+test compound at different concentrations. Binding was performed at room temperature for 20 minutes while continuously inverting the plate. Unbound $^{125}$I-phosphopeptide was separated from SH2-bound radiolabeled peptide by vacuum filtration and washing two times with 100 μL per well of assay buffer. Results are expressed as $IC_{50}$ values in Table 3 below.

Inhibition of DNA Synthesis as Monitored by $^3$H-Thymidine Uptake

DNA synthesis occurs when a cell is exposed to Platelet Derived Growth Factor (PDGF). For PDGF-induced DNA synthesis to occur, c-SRC or another member of the SRC gene family is required. The ability of the SRC SH2 inhibitors of the present invention to block PDGF-stimulated DNA synthesis can be assessed using the protocol set forth below.

Swiss 3T3 cells were grown in 12-well plates for 3 days to approximately 50% confluency. The growth media was removed and replaced with 1.0 mL/well of assay buffer (Dulbecco's Modified Eagle Medium containing 0.2% Bovine Serum Albumin), and incubated for 24 hours to arrest growth.

Test compounds (5 μL) were add at 100 times their final concentration. Methyl sulfoxide was used as a control and levels in all wells kept under 1.0% of DMSO. Cells were then stimulated with growth factor (PDGFbb or Fetal Bovine Serum), and allowed to incubate another 24 hours.

During the final 2 hours of treatment, 5 uL of 0.1 μCi/μL $^3$H-thymidine was added to each well (final=0.5 μCi/well)

After incubation the medium was removed by aspiration, and each well was washed twice with ice-cold phosphate buffered saline (0.5 mL/wash). 0.5 mL ice-cold 5% trichloroacetic acid was added to each well and incubated on ice for a minimum 10 minutes. The trichloroacetic acid solution was removed and each well was washed twice with 0.5 mL ice-cold trichloroacetic acid, and then once with ice-cold water (0.5 mL). 0.5 mL of 2% Sodium Dodecyl Sulfate was added to each well to solubilize the cells and allowed to incubate at room temperature for 10–15 minutes. The solubilized cells were transfered to 20 mL scintillation vials. Each well was washed with 0.5 mL of water and combined with the corresponding scintillation vial. 10 mL of Ready-Gel scintillation cocktail was added to each vial and the vials were then counted in a scintillation counter. Results are shown as percent of $^3$H-thymidine uptake relative to control in Table 4 below.

TABLE 1

Src SH2 Binding Data

| Example | IC$_{50}$, SRC SH2 Binding ($\mu$M) |
|---|---|
| 1 | 2.1 |
| 2 | 2.4 |
| 3 | 2.3 |
| 4 | 6.7 |
| 5 | 5.0 |
| 6 | 1.8 |
| 7 | 2.0 |
| 8 | 5.5 |
| 9 | 6.2 |
| 10 | ~25 |
| 11 | 2.1 |
| 12 | 0.7 |
| 13 | 4.4 |
| 14 | 10.0 |
| 15 | 7.0 |
| 16 | 9.8 |
| 17 | 3.2 |
| 18 | 3.3 |
| 19 | 5.6 |
| 20 | 20 |
| 21 | 5.5 |
| 22 | 8.3 |
| 23 | 6.2 |
| 24 | 7.2 |
| 25 | 7.1 |
| 26 | 9.8 |
| 27 | 8.0 |
| 28 | 12.0 |
| 29 | 8.3 |
| 30 | 5.5 |
| 31 | 3.9 |
| 32 | 9.2 |
| 33 | 9.3 |
| 34 | ~100 |
| 35 | 7.0 |
| 36 | ~30 |
| 37 | 6.7 |
| 38 | 4.1 |
| 39 | 9.7 |
| 40 | 7.0 |
| 41 | 6.6 |
| 42 | ~30 |
| 43 | ~20 |
| 44 | 6.5 |
| 45 | ~50 |
| 46 | 12.5 |
| 47 | ~20 |
| 48 | ~30 |
| 49 | 8.5 |
| 50 | 2.5 |
| 51 | 1.0 |
| 52 | 6.2 |
| 53 | 12.1 |
| 54 | 86 |
| 55 | >100 |
| 56 | 3.8 |
| 57 | 33 |
| 58 | 21 |
| 59 | 1.1 |
| 60 | 1.9 |
| 61 | 16 |
| 62 | 8.3 |
| 63a | 0.3 |
| 63b | 29 |
| 64a | 0.6 |
| 64b | 11 |
| 65 | 9.2 |
| 66 | 3.8 |
| 67 | 1.0 |
| 65 | 1.1 |
| 69 | 2.1 |
| 70 | 24 |
| 71 | 18 |
| 72 | 6.2 |
| 73 | 8.6 |
| 74 | 20 |
| 75 | 7.2 |
| 76 | 34 |

TABLE 2

| Example | SH2-GST | IC$_{50}$ ($\mu$M) |
|---|---|---|
| 1 | Src | 3.9 |
|  | Abl | 7.4 |
|  | Grb2 | >100 |
|  | Syp(N) | >100 |
|  | PLC$\gamma$(C) | >100 |
|  | p85(C) | >100 |
| 5 | Src | ~100 |
|  | Abl | 3.9 |
|  | Grb2 | >100 |
|  | Syp(N) | >100 |
|  | PLC$\gamma$(C) | >100 |
|  | p85(C) | >100 |
| 51 | Src | 2.2 |
|  | Abl | 12.1 |
|  | Grb2 | ~100 |
|  | Syp(N) | ~100 |
|  | PLC$\gamma$(C) | >100 |
|  | p85(C) | >100 |

TABLE 3

Abl SH2 Binding Data

| Example | IC$_{50}$, Abl SH2 Binding ($\mu$M) |
|---|---|
| 5 | 1.7 |
| 10 | 1.6 |
| 11 | 17 |
| 12 | 2.5 |
| 24 | 36 |
| 34 | 42 |
| 35 | >100 |
| 54 | 43 |
| 55 | >100 |
| 57 | 20 |
| 58 | ~60 |
| 59 | 4.5 |
| 60 | 9.7 |
| 61 | ~100 |
| 62 | 44 |
| 63a | 2.0 |
| 63b | 59 |
| 64a | 2.4 |
| 64b | 14 |
| 65 | 24 |
| 66 | 11 |
| 67 | 6.0 |
| 68 | 5.7 |
| 69 | 7.4 |
| 70 | 16 |
| 72 | 28 |
| 73 | 26 |
| 74 | >100 |
| 75 | ~60 |
| 76 | >100 |

TABLE 4

3H-Thymidine Uptake in Swiss 3T3 Cell

| Example | % Uptake Relative to Control |
|---|---|
| 77 | 34% |
| 63a | 73% |
| 55 | 61% |

We claim:

1. A compound of the formula

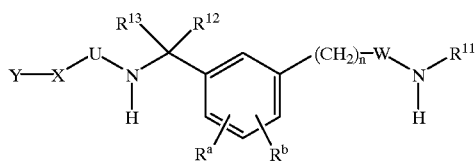

wherein U and W are —C—;

Y is 
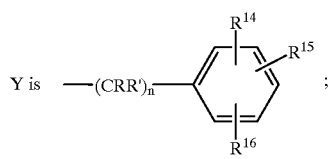

x is 
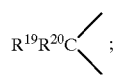

$R^{11}$ is hydrogen, alkyl, —OH, substituted alkyl, or —$NH_2$;

$R^{12}$ is hydrogen or alkyl;

$R^{13}$ is —$(CH_2)_n CO_2 H$, alkyl, —$(CH_2)_n$—aryl, —$(CH_2)_n$-cycloalkyl, hydrogen, substituted cycloalkyl —$(CH_2)_n$—, substituted aryl—$(CH_2)_n$—, or substituted alkyl;

$R^{14}$ is independently —$OPO_3 R^c R^d$, —$CF_2 PO_3 R^c R^d$, —$CH_2 PO_3 R^c R^d$, or —$PO_3 R^c R^d$;

$R^{15}$ and $R^{16}$ are independently hydrogen, alkyl, halogen, —OR, —NRR', —$COCF_3$, —$(CH_2)_n CH_2 OH$, —$(CH_2)_n CO_2 H$, —$(CH_2)_n NRR'$, —$(CH_2)_n CHO$, or —Q—$CH_{2-}(CH_2)_n$—NRR';

$R^{18}$ is —$(CH_2)_n CO_2 R$, hydrogen, alkyl, —$(CH_2)_n$ CONRR', substituted alkyl, or —$(CH_2)_n$-substituted aryl;

$R^{19}$ is hydrogen, RCONR'—, RR'NCONR"—, $RSO_2 NR'$—, $RR'NSO_2 NR"$—, or ROCONR'—;

$R^{20}$ is hydrogen, alkyl, cycloalkyl—$(CH_2)_n$—, substituted alkyl, aryl—$(CH_2)_n$—, —$(CH_2)_n$—$CO_2 H$, substituted cycloalkyl—$(CH_2)_n$—, or substituted aryl—$(CH_2)_n$—;

$R^a$ is hydrogen, halogen, or alkyl;

$R^b$ is hydrogen, alkyl, —OR, —$O(CH_2)_n$-aryl, —NRR', —$O(CH_2)_n$-substituted alkyl, —SR, —$O(CH_2)_n$-substituted aryl, or —$O(CH_2)_n$-cycloalkyl;

$R^c$ and $R^d$ are independently —R, —$CH_2 CH_2 Z$, —$CH_2 CHZ_2$, or —$CH_2 CZ_3$;

Q is —O—, —NH—, —S—, —$CH_2 O$—, —$CH_2 NH$—, or —$CH_2 S$—;

Z is —Cl, —Br, or —F;

R, R', and R" are independently hydrogen, alkyl, cycloalkyl—$(CH_2)_n$—, aryl—$(CH_2)_n$—, —$CH_2$—$(CH_2)_n$—$CO_2 H$, substituted cycloalkyl—$(CH_2)_n$—, substituted alkyl, or substituted aryl—$(CH_2)_n$—; and each n is independently 0 to 5, or the pharmaceutically acceptable salts thereof.

2. A compound according to claim 1 wherein
$R^{13}$, $R^a$, $R^{15}$, and $R^{16}$ are hydrogen;
$R^{12}$ and $R^{11}$ are hydrogen or alkyl;
$R^b$ is —OR, —$O(CH_2)_n$-aryl, —$O(CH_2)_n$substituted aryl, or —$O(CH_2)_n$cycloalkyl; and
$R^{14}$ is —$OPO3 R^c R^d$ or —$CF_2 PO_3 R^c R^d$.

3. A compound according to claim 1 wherein
$R^{19}$ is RCONR'— or RR'NCONR"—;
$R^{20}$, $R^{15}$, $R^{13}$, $R^{11}$, $R^a$, and $R^{16}$ are hydrogen;
$R^{12}$ is alkyl or hydrogen;
$R^b$ is —OR, —$O(CH_2)_n$-aryl, —$O(CH_2)_n$substituted aryl, or —$O(CH_2)_n$cycloalkyl; and
$R^{14}$ is —$OPO_3 R^c R^d$ or —$CF_2 PO_3 R^c R^d$.

4. A method of inhibiting the binding of a protein containing an SH2 domain to a cognate phosphorylated protein, the method comprising administering to a patient in need of SH2 inhibition an SH2 inhibiting amount of a compound of claim 1.

5. The method of claim 4 wherein the protein containing the SH2 domain is Src, Fyn, Lck, Yes, Blk, Lyn, Fgr, Hck, Yrk, or Abl.

6. The method of claim 4 wherein the protein containing the SH2 domain is pp60c-src kinase.

7. The method of claim 4 wherein the cognate phosphorylated protein is PDGF receptor protein, EGF receptor protein, HER2/Neu receptor protein, fibroblast growth factor receptor protein, focal adhesion kinase protein, p130 protein, or p68 protein.

8. The method of claim 4 wherein the patient in need of SH2 inhibition has a cancer in which the building of a SH2 domain to a cognate phosphorylated protein is involved, restenosis, osteoporosis, inflammation, or allergies.

9. A pharmaceutical composition that comprises a compound of claim 1 and a pharmaceutically acceptable carrier.

10. A method of treating a patient having cancer in which the binding of a SH2 domain to a cognate phosphorylated protein is involved, the method comprising administrating to the patient a therapeutically effective amount of a compound of claim 1.

11. A method of treating a patient having restenosis, the method comprising administering to the patient a therapeutically effective amount of a compound of claim 1.

12. A method of treating a patient having osteoporosis, the method comprising administering to the patient a therapeutically effective amount of a compound of claim 1.

13. A method of treating a patient having inflammation, the method comprising administering to the patient a therapeutically effective amount of a compound of claim 1.

14. A method of treating a patient having allergies, the method comprising administering to the patient a therapeutically effective amount of a compound of claim 1.

15. The compound that is:
(S)-Phosphoric acid mono-{4-[2-acetylamino-2-(3-carbamoyl-4-cyclohexylmethoxy-benzylcarbamoyl)-ethyl]-phenyl} ester;
Phosphoric acid mono-(4-{(S)-2-acetylamino-2-[(RS)-1-(3-carbamoyl-4-cyclohexylmethoxy-phenyl)-ethylcarbamoyl]-ethyl}-phenyl) ester;

(S)-Phosphoric acid mono-{4-[2-acetylureido-2-(3-carbamoyl-4-cyclohexylmethoxy-benzylcarbamoyl)-ethyl]-phenyl} ester; or (S)-{4-[2-Acetylamino-2-(3-carbamoyl-4-cyclohexyl-methoxy-benzylcarbamoyl)-ethyl]-phenyl}-difluoro-methyl-phosphonic acid.

16. A compound according to claim 1 wherein $R^{13}$, $R^{11}$, and $R^a$ are hydrogen;

$R^{12}$ is alkyl or hydrogen;

$R^b$ is —OR, —O(CRR')$_n$-aryl, —O(CRR')$_n$ substituted aryl, or —O(CRR')$_n$cycloalkyl; and $R^{17}$ is —OPO$_3$R$^c$R$^d$, —CF$_2$PO$_3$R$^c$R$^d$, or PO$_3$R$^c$R$^d$.

17. The compound that is:

[S-(R*,R*)]- or [S-(R*,S*)]-[(4-{2-Acetylamino-2-[1-(3-carbamoyl-4-cyclohexylmethoxy-phenyl)-ethylcarbamoyl]-ethyl}-phenyl)-difluoro-methyl]-phosphonic acid;

[S-(R*,R*)]- or [S-(R*,S*)]-[(4-{2-Acetylamino-2-[1-(3-carbamoyl-4-cyclohexylmethoxy-phenyl)-ethylcarbamoyl]-ethyl}-phenyl)-difluoro-methyl]-phosphonic acid;

Phosphoric acid mono-[4-(2-acetylamino-2-{1-[3-carbamoyl-4-(2-cyclohexyl-1-methyl-ethoxy)-phenyl]-ethylcarbamoyl}-ethyl)-phenyl] ester;

Phosphoric acid mono-[4-(2-acetylamino-2-{1-[3-carbamoyl-4-(2-cyclohexyl-1-methyl-ethoxy)-phenyl]-ethylcarbamoyl}-ethyl)-phenyl] ester;

(S)-Phosphoric acid mono-(4-{2-acetylamino-2-[(RS)-1-(3-carbamoylmethyl-4-cyclohexylmethoxy-phenyl)-ethylcarbamoyl]-ethyl}-phenyl) ester;

Phosphoric acid mono-(4-{(S)-2-acetylamino-2-[3-carbamoyl-4-(2-cyclohexyl-(RS)-1-methyl-ethoxy)-benzylcarbamoyl]-ethyl}-phenyl) ester;

Phosphoric acid mono-(4-{(S)-2-acetylamino-2-[(RS)-1-(3-carbamoyl-4-cyclohexylmethoxy-phenyl)-2-phenyl-ethylcarbamoyl]-ethyl}-phenyl) ester;

Phosphoric acid mono-[4-((S)-2-acetylamino-2-{(RS)-1-[3-carbamoyl-4-(3,5-dimethyl-benzyloxy)-phenyl]-ethylcarbamoyl}-ethyl)-phenyl] ester;

Phosphoric acid mono-(4-{(S)-2-acetylamino-2-[(RS)-1-(3-carbamoyl-4-cyclohexylmethoxy-phenyl)-butylcarbamoyl]-ethyl}-phenyl) ester;

(S)-Phosphoric acid mono-{4-[2-acetylamino-2-(4-cyclohexylmethoxy-3-hydroxycarbamoyl-benzylcarbamoyl)-ethyl]-phenyl} ester;

(S)-Phosphoric acid mono-{4-[2-acetylamino-2-(4-cyclohexylmethoxy-3-hydrazinocarbonyl-benzylcarbamoyl)-ethyl]-phenyl} ester;

(S)-Phosphoric acid mono-(4-{2-acetylamino-2-[3-carbamoyl-4-(2-ethyl-benzyloxy)-benzylcarbamoyl]-ethyl}-phenyl) ester; or (4-{(S)-2-Acetylamino-2-[(RS)-1- (3-carbamoyl-4-cyclohexylmethoxy-phenyl)-ethylcarbamoyl]-ethyl}-phenyl)-phosphonic acid.

* * * * *